United States Patent
Kodama et al.

(10) Patent No.: US 7,955,807 B2
(45) Date of Patent: Jun. 7, 2011

(54) METHOD OF MEASURING PTX3 WITH HIGH SENSITIVITY

(75) Inventors: Tatsuhiko Kodama, Setagaya-ku (JP); Takao Hamakubo, Komae (JP); Koji Maemura, Bunkyo-ku (JP); Akira Sugiyama, Bunkyo-ku (JP); Hiroko Iwanari, Bunkyo-ku (JP); Isao Kohno, Meguro-ku (JP); Yukio Ito, Kuki (JP)

(73) Assignees: The University of Tokyo, Tokyo (JP); Perseus Proteomics Inc., Tokyo (JP)

( * ) Notice: Subject to any disclaimer, the term of this patent is extended or adjusted under 35 U.S.C. 154(b) by 318 days.

(21) Appl. No.: 12/092,272

(22) PCT Filed: Nov. 10, 2006

(86) PCT No.: PCT/JP2006/322505
§ 371 (c)(1),
(2), (4) Date: May 1, 2008

(87) PCT Pub. No.: WO2007/055340
PCT Pub. Date: May 18, 2007

(65) Prior Publication Data
US 2010/0062449 A1    Mar. 11, 2010

(30) Foreign Application Priority Data

Nov. 11, 2005  (JP) .................................. 2005-326987
Apr. 12, 2006  (JP) .................................. 2006-109443

(51) Int. Cl.
 G01N 33/577  (2006.01)
 G01N 33/549  (2006.01)
 C12P 21/08   (2006.01)
 C07K 16/28   (2006.01)
 C07K 16/18   (2006.01)
(52) U.S. Cl. ... 435/7.1; 435/70.21; 435/810; 530/387.1; 530/388.1; 530/388.24
(58) Field of Classification Search .................. None
See application file for complete search history.

(56) References Cited

U.S. PATENT DOCUMENTS

| | | | |
|---|---|---|---|
| 2004/0137544 A1* | 7/2004 | Latini et al. | 435/7.92 |
| 2008/0261251 A1* | 10/2008 | Mantovani et al. | 435/7.92 |

FOREIGN PATENT DOCUMENTS

| | | |
|---|---|---|
| JP | 7 209293 | 8/1995 |
| JP | 11 1494 | 1/1999 |
| JP | 2000 297098 | 10/2000 |
| WO | 01 25427 | 4/2001 |
| WO | 2005 080981 | 9/2005 |

OTHER PUBLICATIONS

U.S. Appl. No. 10/590,526, filed Aug. 24, 2006, Kodama, et al.
Mariam Klouche, et al., "Modified Atherogenic Lipoproteins Induce Expression of Pentraxin-3 by Human Vascular Smooth Muscle Cells", Atherosclerosis, XP002508603, vol. 175, No. 2, Aug. 2004, pp. 221-228.
Ferruccio Breviario, et al., "Interleukin-1-Inducible Genes in Endothelial Cells", Cloning of a New Gene Related to C-Reactive Protein and Serum Amyloid P Component, The Journal of Biological Chemistry, vol. 267, No. 31, Issue of Nov. 5, pp. 22190-22197, 1992.
Michael S. Rolph, et al., "Atherosclerosis and Lipoproteins" "Rapid Communication Production of the Long Pentraxin PTX3 in Advanced Atheosclerotic Plaques", Arterioscler Thromb Vasc Biol., 22 (5) : e10-14, May 1, 2002.
Kaoru Hatanaka, et al., "Molecular Biology of Acute Phase Proteins Pentaxin Family", Arterial Sclerosis 24(7.8): pp. 375-380, 1996.
Fausto Fazzini, et al., "PTX3 in Small-Vessel Vasculitides", An Independent Indicator of Disease Activity Produced at Sites of Inflammation, Arthritis & Rheumatism, vol. 44, No. 12, Dec. 2001, pp. 2841-2850.
Giuseppe Peri, et al., "PTX3, a Prototypical Long Pentraxin, is an Early Indicator of Acute Myocardial Infarction in Humans", Downloaded from circ.ahajournals.org by on May 30, 2008.

* cited by examiner

*Primary Examiner* — Phuong Huynh
(74) *Attorney, Agent, or Firm* — Oblon, Spivak, McClelland, Maier & Neustadt, L.L.P.

(57) ABSTRACT

To provide a method of determining vasculopathy, which is a risk factor of myocardial infarction, angiopathic dementia, etc., at an early stage thereof (i.e., mild vasculopathy). The present invention provides a method of determining the severity of mild vasculopathy, including determining PTX3 level in an assay sample by use of an anti-PTX3 monoclonal antibody.

20 Claims, 14 Drawing Sheets

METHOD OF MEASURING PTX3 WITH HIGH SENSITIVITY

TECHNICAL FIELD

The present invention relates to a method of determining vasculopathy including high-sensitivity detection of blood PTX3.

BACKGROUND ART

PTX3, which is also called pentraxin, pentaxin, TSG-14 or MPTX3, is a secretion protein belonging to the pentraxin family and is known to be expressed in human umbilical cord vessel endothelium cells stimulated with interleukin 1 (IL-1) (Non-Patent Document 1).

The pentraxin family includes C-reactive protein (CRP) and serum amyloid P component (SAP), which are known as inflammation-related proteins. Pentraxin is also called long pentraxin, and CRP is also called short pentraxin. Thus, pentraxin is implicative of the presence of a CRP sequence region in the structure thereof, and is predicted to function as an inflammation-related protein. Differing from CRP and SAP, PTX3 is not susceptible to induction by IL-6. The type of cells expressing PTX3 protein differs from those of CRP and SAP. These features indicate that PTX3 also has a function different from that of CRP and SAP (Non-Patent Documents 2 and 3).

In patients of acute myocardial infarction, which is considered a type of inflammation reaction, some PTX3-related findings have been obtained. For example, elevated blood PTX3 level was observed, and PTX3 was detected in plaques present in an advanced arteriosclerotic lesion (possible indicator for small vasculitis) by immunostaining. Thus, PTX3 has been thought to participate in inflammation (Non-Patent Documents 4 to 6).

The term "inflammation" refers to a wide range of types of inflammation including dermatitis and those of a variety of organs. Among them, vasculitis may cause a serious disease such as heart disease or cerebral disease.

Regarding heart disease, risk factors for acute myocardial infarction include high total blood cholesterol, hypertension, diabetes, obesity, and habitual smoking, and efforts to prevent acute myocardial infarction have been made through control of these risk factors. However, according to the "annual dynamic population statistics" (by the Japanese Ministry of Health, Labor, and Welfare (2004)), 15.5% of Japanese die from heart disease, making heart disease the second leading cause of death among Japanese. A detailed study has revealed that most cases of fatal heart diseases are heart failure and acute myocardial infarction, which account for 5.0% and 4.3% of deaths, respectively. These heart diseases are known to be mainly caused by coronary lesion. In addition to heart failure and acute myocardial infarction, examples of complications of coronary lesions include angina and sudden death caused by arrhythmia. In the United States, the American Heart Association has reported that about 12,000,000 or more American people have a clinical history of a certain coronary disease. Thus, coronary lesion is the leading cause of death among Americans, and accounts for about ⅓ of deaths every year.

Examples of cerebral disease include dementia from vasculopathy, and aspirin has been used a prophylactic measure.

Although there are some diagnostic methods for serious pathological conditions in the heart and the brain (e.g., myocardial infarction and cerebral infarction), there has not been known a method for diagnosing mild forms of vasculitis or other vasculopathy.

Conventionally, PTX3 has been determined through an ELISA-based method disclosed in Non-Patent Documents 4 to 6. It is described that PTX3 level reaches its maximum (0.5 to 22 ng/mL) 7.5 hours after myocardial infarction, and then drastically decreases to 0.5 to 2.5 ng/mL, which is a level exhibited by healthy people probably not suffering heart disease. Thus, conventional determination of PTX3 level indicates that the blood PTX3 protein level increases during myocardial infarction attack. However, heretofore, modification in PTX3 protein level at a stage before the onset of myocardial infarction has not yet been elucidated.

Non-Patent Document 1: Breviorio et al.: J. Biol. Chem., 267(31), 22190-7 (1992)
Non-Patent Document 2: J. Biol. Chem., 267(31), 22190-7 (1992)
Non-Patent Document 3: Domyaku Koka (Arteriosclerosis), 24(7-8), 375-80 (1996)
Non-Patent Document 4: Arthritis and Rheumatism, 44/12 (2841-50), 2001
Non-Patent Document 5: Circulation, 102, 636-41 (2000)
Non-Patent Document 6: Arterioscler. Thromb. Vasc. Biol. 2002; 22: e10-e14
Patent Document 1: WO 2005/080981 pamphlet

DISCLOSURE OF THE INVENTION

Problems to be Solved by the Invention

As disclosed in the pamphlet of WO 2005/080981, the inventors of the present invention previously participated in the development of a new PTX3 measuring system, and successfully diagnosed unstable angina through assaying blood PTX3 level, whereby the correlation of the severity of vasculopathy with PTX3 level was established.

If mild vasculopathy can be determined before the onset of myocardial infarction, angiopathic dementia, etc. or at an initial stage of the pathological conditions; in other words, if mild vasculopathy can be determined before expression of an initial symptom of a heart disease, a cerebral disease, etc. or at an initial stage of the expressed symptom, early treatment or prevention thereof can be realized. As a result, death rate attributed to circulatory diseases and metabolism-related diseases can be lowered, and the QOL of the patients can be enhanced.

Thus, an object of the present invention is to provide a method of determining vasculopathy, which is a risk factor of myocardial infarction, angiopathic dementia, etc., at an early stage thereof; namely, mild vasculopathy.

Means for Solving the Problems

PTX3 is a protein consisting of a single-strand polypeptide having 381 amino acid residues in the full length (hereinafter, the protein may be referred to as "PTX3 protein" or "full-length PTX3," SEQ ID NOs: 1 and 2). The amino acids 1 to 17 in SEQ ID NO: 2 form a signal peptide. When PTX3 protein is secreted from cells and matured, the signal peptide is cleaved from PTX3 protein. The N-terminal region of PTX3 protein corresponds to amino acids 18 to 178 in SEQ ID NO: 2 (hereinafter referred to as PTX3 N-terminal region), and the C-terminal region thereof corresponds to amino acids 179 to 381 in SEQ ID NO: 2 (hereinafter referred to as PTX3 C-terminal region). The C-terminal region is called a pentraxin domain, which has high homology to CRP and SAP belonging to the pentraxin family.

There have been reported some antibodies recognizing PTX3, and examples thereof include the following:

16B5 (Bottazzi et al., J. of Biol. Chem. 272(52), 32817-23, 1997); 1C8 (Bottazzi et al., J. of Biol. Chem. 1997, 272(52), 32817-32823); MNB4 (Peri et al., Circulation 2000, 102, 636-641); MNB6 (Peri et al., Circulation 2000, 102, 636-641); MNB10 (WO2005/106494, accession No. ABC PD04001); Pen-3 (WO2005/106494, accession No. ABC PD01004); PPMX0101 (WO2005/080981, accession No. FERM P-19697); PPMX0102 (WO2005/080981, accession No. FERM BP-10326); PPMX0112 (WO2005/080981); and PPMX0148 (WO2005/080981).

Among known PTX3-recognizing antibodies, MNB4 and 16B5 are reported to recognize an N-terminal region and a C-terminal region, respectively (Comozzi et al., J. Biol. Chem., 281(32), 22605-22613, 2006). In this study, epitope mapping was carried out through reaction of an antibody with a synthetic peptide consisting of 12 or 13 amino acid residues, and MNB4 and 16B5 were both found to recognize a short peptide having 12 or 13 amino acid residues. Such an antibody recognizing a short peptide is considered to recognize an epitope not attributed to a conformational structure.

In order to attain the object of the present invention; i.e., to provide a method of determining mild vasculopathy, a monoclonal antibody recognizing a conformational epitope of PTX3 has been developed, whereby sensitivity and accuracy of PTX3 assay has been successfully improved. Furthermore, through analysis of patients having mild vasculopathy (including those suffering stable angina and chest pain) by use of the monoclonal antibody, a significant difference has been found in PTX3 levels between healthy subjects and those having mild vasculopathy.

Accordingly, the present invention provides a method of determining the severity of mild vasculopathy, including measuring PTX3 level in an assay sample by use of an anti-PTX3 monoclonal antibody.

The present invention also provides a method of determining the severity of mild vasculopathy, wherein the anti-PTX3 monoclonal antibody is a monoclonal antibody or a fragment thereof recognizing a conformational epitope of PTX3.

The present invention also provides a diagnostic agent for determining the severity of mild vasculopathy, containing an anti-PTX3 monoclonal antibody or a fragment thereof.

The present invention also provides an anti-PTX3 monoclonal antibody or a fragment thereof recognizing a conformational epitope of PTX3.

The present invention also provides a hybridoma producing an anti-PTX3 monoclonal antibody or a fragment thereof recognizing a conformational epitope of PTX3.

Effects of the Invention

According to the present invention, mild vasculopathy can be determined before the onset of myocardial infarction, angiopathic dementia, etc. or at an initial stage of the pathological conditions after the onset. Therefore, aggravation of the vasculopathy caused by a serious heart disease, a cerebral disease, etc. can be prevented or treated at an early stage.

BEST MODE FOR CARRYING OUT THE INVENTION

Figure 1:
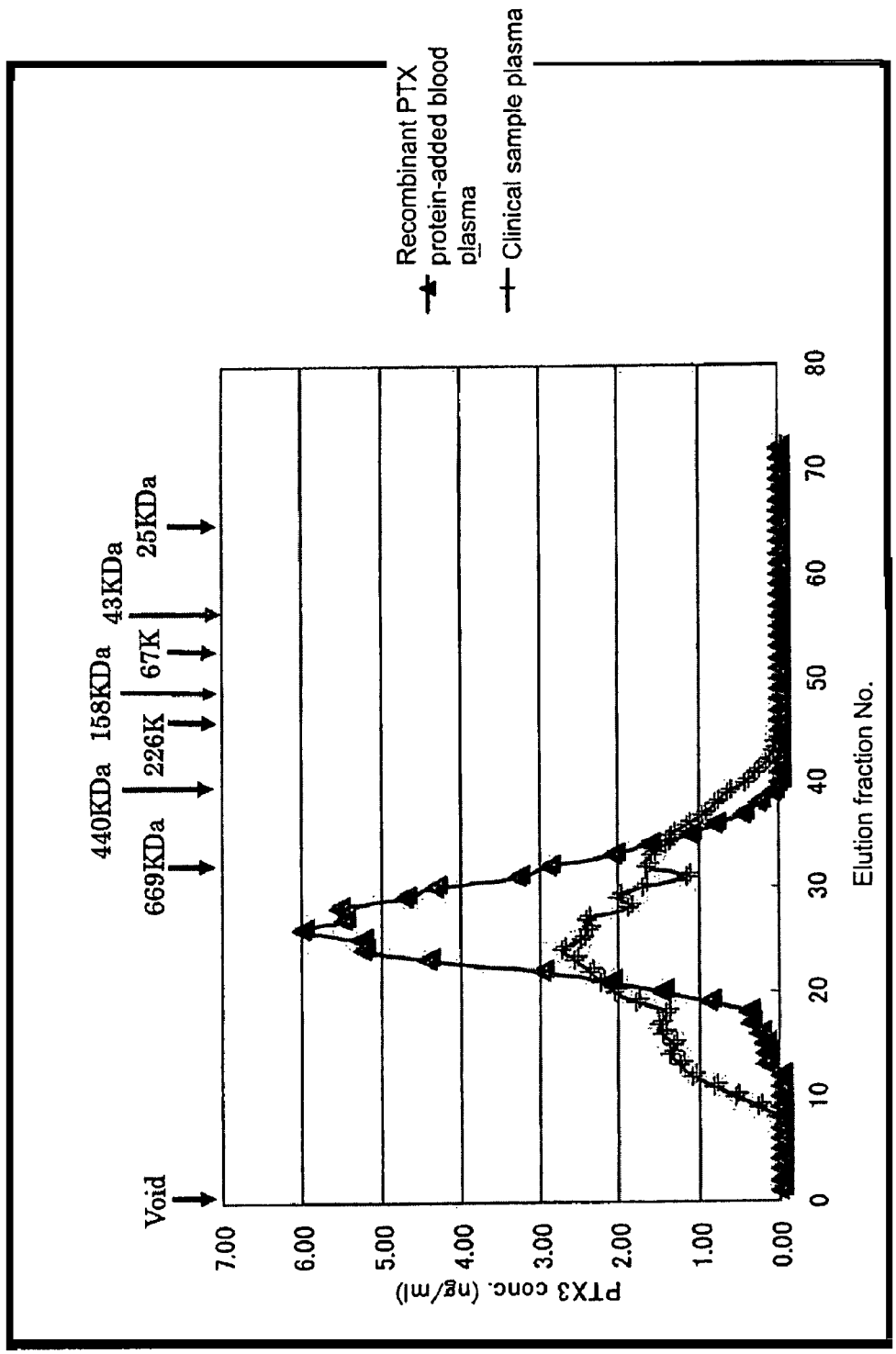
[FIG. 1] Results from gel filtration of recombinant PTX3 protein prepared in Example 3 and PTX3 protein present in a clinical sample (Example 4).

As used herein, the term "measurement" refers to both quantitative and non-quantitative measurement. Examples of the non-quantitative measurement include measurement to simply check the presence or absence of PTX3 protein, measurement to determine the presence or absence of PTX3 protein in a predetermined amount or more, and measurement to determine the amount of PTX3 protein as compared with other samples (e.g., a control sample). Examples of the quantitative measurement include determination of PTX3 protein level and determination of the amount of PTX3 protein. The nucleotide sequence of mRNA of PTX3 gene is represented by SEQ ID NO: 1, and the amino acid sequence of PTX3 protein is represented by SEQ ID NO: 2.

No particular limitation is imposed on the type of the assay sample, so long as the sample may contain PTX3 protein. Preferably, the sample is obtained from an organism such as a mammal, more preferably from a human. Specific examples of the assay sample include blood, interstitial fluid, plasma, extravascular fluid, cerebrospinal fluid, synovial fluid, pleural fluid, serum, lymph, saliva, and urine. Of these, blood, serum, and plasma are preferred. Further, assay samples such as a solution from cell culture derived from an organism body also fall within the scope of the assay sample of the present invention.

Vasculopathy progresses to cause a serious disease, via disorders of vascular endothelial cells, migration of smooth muscle cells of the vascular media, recruitment of macrophages and formation of foam cells, adhesion of thrombi, plaque formation, fibrosis of blood vessels, and breakage of plaques.

In the present invention, "vasculopathy" includes vascular disorders caused by hyperlipemea, heart disease, cerebral disease, hypertension, diabetes, obesity, and smoking. In particular, the term "mild vasculopathy" refers to vascular disorders occurring before or at the onset of an initial symptom of a heart disease or a cerebral disease caused by vasculopathy. Examples of the disease (pathological condition) accompanying mild vasculopathy include chest pain and stable angina. These diseases are developed from coronary lesion, and the diseases is milder as a fewer number of blood vessels have lesion.

In the present invention, the severity of vasculopathy refers to the level of disorders accompanied by the progression of the vasculopathy as described above. In other words, the severity of the progression of the vasculopathy as described above, which reflects the probability of generating the breakage of plaques, is indicated by the following pathological histological parameters: (a) lipid core size, (b) thickness of fibrous cap, (c) shear stress, and (d) infiltration extent of inflammation cells. The probability of generating the breakage of plaques is increased with the increase of (a), reducing (b), the increased of (c), or the increased of (d). Thus, the severity of vasculopathy in the present invention reflects the level of the aforementioned (a) to (d).

In the method of the present invention, PTX3 protein is preferably measured through immunological assay employing an anti-PTX3 antibody. The assay employing an anti-PTX3 antibody will next be described in detail.

1. Production of an Anti-PTX3 Antibody

No particular limitation is imposed on the anti-PTX3 antibody employed in the present invention, so long as the antibody specifically binds to PTX3 protein. Preferably, the antibody recognizes a conformational epitope of PTX3 protein. More preferably, the antibody does not recognize a fragmented N-terminal or C-terminal polypeptide of PTX3, but recognizes a conformational epitope of PTX3 protein. Still more preferably, the antibody exhibits high binding affinity to a conformational structure of PTX3 and does not cross-react with CRP or SAP. Most preferred antibodies are PPMX 0104 (FERM BP-10719) and PPMX 0105 (FERM BP-10720). Hybridomas PPMX 0104 (FERM BP-10719) and PPMX 0105 (FERM BP-10720) have been deposited under the terms of the Budapest Treaty at the International Patent Organism Depositary, National Institute of Advanced Industrial Science and Technology, AIST Tsukuba Central 6, 1-1, Higashi 1-chome, Tsukuba-shi, Ibaraki-ken 305-8566, Japan.

The term "conformational epitope" as used herein refers to all epitopes in the full-length PTX3 protein excluding those recognized as a primary structure, namely epitopes of the full-length PTX3 recognized as a secondary, tertiary, or quaternary structure. Meanwhile, the conformational structure of protein is known to hierarchically include primary, secondary, tertiary, and quaternary structures (Medical Dictionary, Published by Nanzando, revised 17 edition (1990)).

As described in the Examples hereinbelow, the antibody of the present invention is preferably an antibody which recognizes PTX3 in a non-reduced state, does not react with a PTX3 fragment, and recognizes a conformational epitope of PTX3 protein. Thus, such an antibody strongly can react with intact PTX3 to thereby discriminate PTX3 maintaining a higher-order structure in vivo from other proteins.

No particular limitation is imposed on the origin, type (monoclonal, polyclonal), and morphology of the anti-PTX3 antibody employed in the present invention. Specifically, known antibodies such as a mouse antibody, a rat antibody, a human antibody, a chimera antibody and a humanized antibody may be employed. Although these antibodies may be polyclonal, monoclonal antibodies are preferred.

The anti-PTX3 antibody immobilized on a substrate and the anti-PTX3 antibody labeled with a labeling substance may recognize the same epitope of the PTX3 molecule. Preferably, these antibodies recognize different epitopes.

The anti-PTX3 antibody employed in the present invention may be obtained through a known means as a polyclonal or monoclonal antibody. The anti-PTX3 antibody employed in the present invention is particularly preferably a mammal monoclonal antibody. The mammal monoclonal antibody includes that produced from a hybridoma and that produced by a host genetically transformed by an expression vector containing an antibody gene.

Generally, the hybridoma producing a monoclonal antibody may be produced through a known technique in the following procedure. Specifically, PTX3 is employed as a sensitizing antigen, and immunization is performed through a known method. The thus-obtained immunocytes are fused with known parent cells through a routine cell fusion method. Through a routine screening method, cells producing a monoclonal antibody can be screened.

Specifically, the monoclonal antibody may be produced in the following procedure.

Firstly, PTX3 employed as a sensitizing antigen for producing the antibody is obtained through purification of a supernatant of a culture of available cells. Alternatively, PTX3 may also be obtained through a method disclosed in JP2002-503642.

The thus-purified PTX3 protein or a fragment thereof is employed as a sensitizing antigen.

No particular limitation is imposed on the mammal to be immunized by the sensitizing antigen, and the mammal is preferably selected in consideration of adaptability to parent cells employed in cell fusion. Generally, rodents such as mice, rats and hamsters, rabbits, and monkeys are employed.

Immunization of an animal with a sensitizing antigen is performed through a known method. For example, in a generally employed method, the sensitizing antigen is administered to a mammal through intraperitoneal or subcutaneous injection. More specifically, a sensitizing antigen is diluted with and suspended in an appropriate amount of PBS (Phosphate-Buffered Saline), physiological saline or a similar medium, and if required, an appropriate amount of a conventional adjuvant (e.g., Freund's complete adjuvant) is added to the suspension. The mixture is emulsified and administered to the mammal several times per day every 4 to 21 days. Upon immunization with a sensitizing antigen, an appropriate carrier may also be used. Particularly when a partial peptide having a small molecular weight is employed as a sensitizing antigen, the partial peptide is preferably bound to a carrier protein such as albumin or keyhole lympet hemocyanin for immunization.

The mammal is immunized in the above manner. After observing that the serum antibody level has been elevated to a desired level, immunocytes are collected from the mammal, and the collected cells are subjected to cell fusion. Among immunocytes, spleen cells are particularly preferred.

The parent cells to be fused with the aforementioned immunocytes are myeloma cells of a mammal. The myeloma cells to be preferably employed are known cell strains such as P3(P3x63Ag8.653) (J. Immnol. (1979) 123, 1548-1550), P3x63Ag8U.1 (Current Topics in Microbiology and Immunology (1978) 81, 1-7), NS-1 (Kohler, G. and Milstein, C. Eur. J. Immunol. (1976) 6, 511-519), MPC-11 (Margulies, D. H. et al., Cell (1976) 8, 405-415), SP2/0 (Shulman, M. et al., Nature (1978) 276, 269-270), FO (de St. Groth, S. F. et al., J. Immunol. Methods (1980) 35, 1-21), S194 (Trowbridge, I. S., J. Exp. Med. (1978) 148, 313-323), and R210 (Galfre, G. et al., Nature (1979) 277, 131-133).

Basically, cell fusion between the aforementioned immunocytes and the myeloma cells may be performed through a known method; for example, a method of Kohler, G. and Milstein, C., disclosed in Methods Enzymol. (1981) 73, 3-46.

More specifically, the cell fusion is performed in a conventional nutritive culture solution in the presence of a cell fusion promoting agent. Examples of the fusion promoting agent to be employed include polyethylene glycol (PEG) and Sendai virus (HVJ). In addition, in order to enhance fusion efficiency, a fusion aid such as dimethyl sulfoxide may be optionally added.

The ratio of immunocytes to myeloma cells may be predetermined arbitrarily. For example, immunocytes are preferably used in an amount 1 to 10 times of myeloma cells. Examples of the culture solution employable in the cell fusion include RPMI1640 culture solution and MEM culture solution, which are suitable for proliferation of myeloma cell strains, and other conventional culture solutions employed in such cell culturing. In addition, serum supplements such as fetal calf serum (FCS) may be used in combination.

In the cell fusion, predetermined amounts of the immunocytes and the myeloma cells are sufficiently mixed together in the culture liquid, and a 30-60% (w/v) solution of polyethylene glycol (PEG) (e.g., average molecular weight: about 1,000 to 6,000), which has been heated to about 37° C. in advance, is added to the cell mixture, whereby target hybridomas are formed. Subsequently, an appropriate culture solution is successively added and the mixture was repeatedly centrifuged to remove supernatant in order to remove substances undesirable for growth of the hybridoma, such as a cell fusion agent.

The thus-obtained hybridomas are selected through culturing in a conventional selective culture solution such as HAT culture liquid (culture solution containing hypoxanthine, aminopterin, and thymidine). The culturing in the HAT culture solution is continued for a period of time sufficient to kill cells other than target hybridomas (non-fused cells), generally for several days to several weeks. Subsequently, screening and mono-cloning of hybridomas producing the target antibody is performed through a conventional limiting dilution method.

Screening and mono-cloning of the target antibody may be performed through a known screening method based on antigen-antibody reaction. For example, an antigen is immobilized on a carrier such as polystyrene beads or a 96-well microtiter plate, and a culture supernatant of the hybridomas is caused to react with the antigen. After washing the carrier, an enzyme-labeled second antibody or a similar antibody is caused to react. Through this procedure, presence of an antibody which reacts with the sensitizing antigen is detected in the culture supernatant. The hybridomas producing the target antibody can be cloned through the limiting dilution method or a similar method. In this case, the antigen may be an antigen which has been employed in immunization.

Instead of the method for producing the hybridoma through immunization of an animal other than human with an antigen, a target human antibody exhibiting binding activity to PTX3 may be obtained through another method (see, JP01-59878). In the method, human lymphocytes are sensitized in vitro with PTX3, and sensitized lymphocytes are fused with human myeloma cells, which have permanent cell division performance. Still alternatively, PTX3 (antigen) is administered to a transgenic animal having a complete repertory of human antibody genes, whereby cells producing the anti-PTX3 antibody are obtained. The cells are immortalized, and a human antibody with respect to PTX3 is obtained (see, WO94/25585, WO93/12227, WO92/03918 and WO94/02602).

The thus-produced hybridomas producing a monoclonal antibody can be subcultured in a conventional culture solution, and stored in liquid nitrogen for a long period of time.

When a monoclonal antibody is obtained from the hybridomas, the hybridomas are cultured through a conventional method, and the culture supernatant is collected. Alternatively, the hybridomas are administered to a mammal adaptable to the hybridomas and proliferated in the body, and the monoclonal antibody is collected with the abdominal dropsy. The former method is suitable for producing a high-purity monoclonal antibody, whereas the latter method is suitable for mass production of a monoclonal antibody.

When an antibody fragment is employed, a gene encoding the fragment is constructed, and the gene is introduced into an expression vector, followed by expressing in appropriate host cells.

So long as a full-length protein encoded by a PTX3 gene or a fragment thereof can be recognized, these antibodies may be a low-molecule antibody such as an antibody fragment or a modified product of the antibodies. Examples of antibody fragments include Fab, Fab', F(ab')$_2$, Fv and Diabody. For producing such antibody fragments, an antibody is treated with an enzyme such as papain or pepsin, to thereby digest the Fc domain of IgG. Alternatively, a gene coding for these antibody fragments is constructed; the gene is introduced to an expression vector; and the vector is expressed in appropriate host cells (see, for example, Co, M. S. et al., J. Immunol. (1994) 152, 2968-2976; Better, M. and Horwitz, A. H., Methods Enzymol. (1989) 178, 476-496; Pluckthun, A. and Skerra, A., Methods Enzymol. (1989) 178, 497-515; Lamoyi, E., Methods Enzymol. (1989) 121, 652-663; Rousseaux, J. et al., Methods Enzymol. (1986) 121, 663-669; and Bird, R. E. and Walker, B. W., Trends Biotechnol. (1991) 9, 132-137).

The thus-prepared antibody is isolated from a cell or a host animal, and may be purified to a homogeneous condition. Isolation and purification of the antibody employed in the present invention may be performed by means of an affinity column. Examples of protein A columns include Hyper D, POROS, and Sepharose F. F. (product of GE Healthcare). However, no particular limitation is imposed on the isolation/purification method, so long as it is generally employed for isolating and purifying protein. The antibody may be isolated and purified through an appropriate combination of a chromatography column other than the aforementioned affinity columns, a filter, ultrafiltration, salting out, dialysis, etc. (Antibodies: A Laboratory Manual. Ed Harlow, David Lane, Cold Spring Harbor Laboratory, 1988).

As a modified product of an antibody, an anti-PTX3 antibody, which is bound to a variety of molecules such as a labeling substance, may also be employed. In the present invention, the term "antibody" also includes such antibody modified products. These antibody modified products may be obtained through chemical modification of the obtained antibody. Notably, the method for modifying antibodies has been well established in the art.

2. Measurement of PTX3

No particular limitation is imposed on the method of detecting PTX3 protein contained in an assay sample. However, PTX3 is preferably detected through immunoassay by use of an anti-PTX3 antibody. Examples of immunoassay include radioimmunoassay, enzyme immunoassay, fluoroimmunoassay, emission immunoassay, immunoprecipitation, immunonephelometry, Western blotting, immunostaining, and immunodiffusion. Of these, enzyme immunoassay is preferred, with enzyme-linked immunosorbent assay (ELISA) (e.g., sandwich ELISA) being particularly preferred. The aforementioned immunoassay methods including ELISA may be carried out through a technique known in the art.

In one general detection method employing an anti-PTX3 antibody, an anti-PTX3 antibody is immobilized on a support, and an assay sample is added to the support. Through incubation, PTX3 protein is bound to the anti-PTX3 antibody. After washing the support, PTX3 protein bound to the support by the mediation of the anti-PTX3 antibody is detected, whereby PTX3 protein contained in the assay sample is detected.

Examples of the support employed in the present invention include supports made of insoluble polysaccharide such as agarose or cellulose; synthetic resin such as silicone resin, polystyrene resin, polyacrylamide resin, nylon resin or polycarbonate resin; or insoluble material such as glass. In use, these supports may be in the form of beads or a plate. In the case of beads, a column filled with the beads may be employed. In the case of plate, a multi-well plate (e.g., 96-well multi-well plate), a biosensor chip, etc., may be employed. Immobilization of the anti-PTX3 antibody on the support may be carried out through a conventional method such as chemical binding or physical adsorption. Any commercially available supports may be employed.

Generally, binding of PTX3 protein to the anti-PTX3 antibody is performed in a buffer. Examples of the buffer employed include phosphate buffer, Tris buffer, citrate buffer, borate salt buffer, and carbonate salt buffer. Incubation is performed under generally employed conditions; for example, 4° C. to room temperature for one hour to 24 hours. After incubation, the support is washed. No particular limitation is imposed on the washing solution, so long as it does not impede binding of PTX3 protein to the anti-PTX3 antibody. For example, a buffer containing a surfactant such as Tween 20 is employed.

In the method of measuring PTX3 protein according to the present invention, a control sample may be placed in addition to an assay sample for detection of PTX3 protein. Examples of the control sample include a negative control sample containing no PTX3 protein and a positive control sample containing PTX3 protein. In the case where control samples are employed, analytical results obtained by the negative control sample containing no PTX3 protein or those obtained by the positive control sample containing PTX3 protein are compared, whereby PTX3 protein present in the assay sample can be detected. In an alternative method, a series of control samples having stepwise-graded concentrations are prepared. Through analysis of these control samples, a standard curve is obtained from the detection data. With reference to the standard curve, PTX3 protein contained in an assay sample can be quantitatively detected.

In one preferred embodiment, PTX3 protein bound to the support by the mediation of an anti-PTX3 antibody is measured by use of an anti-PTX3 antibody labeled with a labeling substance.

For example, an assay sample is brought into contact with the anti-PTX3 antibody immobilized on the support. After washing the support, PTX3 protein is detected by a labeled antibody which specifically recognizes PTX3 protein.

Labeling of the anti-PTX3 antibody may be performed through a generally known method. Labeling substances such as a fluorescence dye, an enzyme, a co-enzyme, a chemoluminescence substance, a radioactive substance, etc., which are known in the art as labeling substances, may be employed. Specific examples include radioisotopes (e.g., $^{32}P$, $^{14}C$, $^{125}I$, $^{3}H$, and $^{131}I$), fluorescein, rhodamine, dansyl chloride, umbelliferone, luciferase, peroxidase, alkaline phosphatase, β-galactosidase, β-glucosidase, horseradish peroxidase, glucoamylase, lyzozyme, saccharide oxidase, microperoxidase, and biotin. When biotin is used as a labeling substance, enzyme (e.g., alkaline phosphatase)-bound avidin is preferably added after addition of biotin-labeled antibody. Binding of the labeling substance to the anti-PTX3 antibody may be performed through a known method such as the glutaraldehyde method, the maleimide method, the pyridyldisulfide method, or the periodic acid method.

No particular limitation is imposed on the antibody enzymatic labeling method, and examples include the hinge method and the non-hinge method. In the hinge method, a thiol group is formed through reduction of a disulfide bond present in a so-called hinge region in F(ab')$_2$ moiety (moiety having antigen-binding capacity) of an antibody IgG, and Fab' is bound to an enzyme molecule by the mediation of the thiol group. In the non-hinge method, a reaction group of the antibody employed is not specified, but, in many cases, the antibody molecule is bound to an enzyme molecule by the mediation of an amino group of the antibody.

In a specific procedure, a solution containing an anti-PTX3 antibody is added to a support such as a plate, thereby immobilizing the anti-PTX3 antibody on the support. After washing of the plate, the antibody is blocked by BSA, gelatin, albumin, etc. in order to prevent non-specific binding of protein to the antibody. The plate is washed again, and an assay sample is added to the plate. After incubation, the plate is washed, and a labeled anti-PTX3 antibody is added. After incubation for an appropriate time, the plate is washed again, and a labeled anti-PTX 3 antibody remaining on the plate is detected. Detection may be performed through a method known in the art. For example, in the case in which the labeling substance is a radioactive substance, the antibody can be detected through liquid scintillation or the RIA method. When the labeling substance is an enzyme, a substrate is added, and enzymatic change in the substrate, indicated by, for example, coloring, can be detected by means of an absorptiometer. Examples of the substrate include diammonium 2,2-azinobis(3-ethylbenzothiazoline-6-sulfonate) (ABTS), 1,2-phenylenediamine(o-phenylenediamine), and 3,3',5,5'-tetramethylbenzidine (TMB). When the labeling substance is a fluorescence substance, the antibody can be detected by means of a fluorescence meter.

In a particularly preferred embodiment of the method of measuring PTX3 protein of the present invention, an Fc region of the antibody IgG, which does not exhibit antigen-binding capacity, is removed, and the antibody is labeled in accordance with the method as described in relation to the enzymatic labeling method for an assay antibody in Example 17. The thus-labeled antibody is employed.

In a specific procedure, a solution containing an anti-PTX3 antibody is added to a support such as a plate, thereby immobilizing the anti-PTX3 antibody on the support. After washing of the plate, the antibody is blocked by BSA or a similar substance in order to prevent non-specific binding of protein to the antibody. The plate is washed again, and an assay sample is added to the plate. After incubation, the plate is washed, and an anti-PTX3 antibody directly labeled with peroxidase is added. After incubation for an appropriate time, the plate is washed again, and a substrate specific to the enzyme is added. PTX3 protein is detected by an index such as enzymatic change in the substrate.

Another embodiment of the method of measuring PTX3 protein of the present invention is a method using at least one primary antibody specifically recognizes PTX3 protein and at least one secondary antibody specifically recognizes the primary antibody.

In a specific procedure, an assay sample is brought into contact with at least one anti-PTX3 antibody immobilized on the support. After incubation, the support is washed. PTX3 protein remaining after washing is detected by a primary anti-PTX3 antibody and at least one secondary antibody specifically recognizes the primary antibody. In this case, the secondary antibody is preferably labeled with a labeling substance.

Still another embodiment of the method of measuring PTX3 protein of the present invention is a detection method employing coagulation. In the method, PTX3 can be detected by a support sensitized by an anti-PTX3 antibody. No particular limitation is imposed on the type of the carrier which sensitizes the antibody, and any carrier may be employed, so long as the carrier is insoluble, causes no non-specific reaction, and is stable. For example, latex particles, bentonite, collodion, kaolin, fixed sheep erythrocytes, etc. may be employed. Of these, latex particles are preferably employed. Examples of employable latex particles include polystyrene latex particles, styrene-butadiene copolymer latex particles, and polyvinyltoluene latex particles. Of these, polystyrene latex particles are preferably employed. Sensitized particles and a sample are mixed together, and the mixture is stirred for a predetermined period of time. When the amount of anti-PTX3 antibody contained in the sample increases, the extent of particle coagulation increases. Thus, PTX3 can be detected through visual observation of coagulates. Alternatively, turbidity increased by coagulation is measured by means of a spectrophotometer or a similar device, to thereby detect PTX3.

Yet another embodiment of the method of measuring PTX3 protein of the present invention is a method employing a biosensor on the basis of surface plasmon resonance. The biosensor employing surface plasmon resonance enables real-time observation of protein-protein interaction as a surface plasmon resonance signal by use of a small amount of protein without labeling. For example, through employment of a biosensor such as BIA core (product of Pharmacia), binding between PTX3 protein and an anti-PTX3 antibody can be detected. Specifically, an assay sample is brought into contact with a sensor chip on which an anti-PTX3 antibody has been immobilized, whereby PTX3 protein bound to the anti-PTX3 antibody can be detected as change in a resonance signal.

The measuring method of the present invention may be automated by use of a variety of automated inspection apparatuses. Thus, a large number of samples may be assayed simultaneously.

An object of the present invention is to provide a diagnostic agent for determining the severity of vasculopathy. The diagnostic agent contains at least an anti-PTX3 antibody. As used herein, the term "diagnostic agent" also encompasses a kit. When the diagnostic agent is used on the basis of the ELISA method, the drug may contain a support for immobilizing an antibody. Alternatively, an antibody may be bound to the support in advance. When the diagnostic agent is used on the basis of the coagulation method employing a support made of latex, the drug may contain an antibody-adsorbed support. In addition, the diagnostic agent may further optionally contain a blocking solution, reaction solution, reaction-terminating solution or reagents for treating samples.

EXAMPLES

The present invention will next be described in detail by way of Examples, which should not be construed as limiting the invention thereto.

Example 1

Cloning of PTX3

Cloning of a sequence including a full-length ORF region of PTX3 was performed. Single-strand cDNA of a human umbilical cord vessel endothelium cell (HUVEC) is synthesized from mRNA by use of reverse transcriptase. Synthesis of cDNA is performed by use of a kit such as AMV Reverse Transcriptase First-strand cDNA Synthesis Kit (product of Seikagaku Kogyo). Synthesis and amplification of cDNA may be performed through a 5'-RACE method (Frohman, M. A. et al., Proc. Natl. Acad. Sci. USA (1988) 85, 8998-9002, Belyaysky, A. et al., Nucleic Acids Res. (1989) 17, 2919-2932) with PCR and 5'-Ampli FINDER RACE Kit (product of Clontech) or other methods. Through PCR employing primers PTX3-F (KpnI) (SEQ ID NO: 3) and PTX3-R (BamHI) (SEQ ID NO: 4) which had been constructed from GenBank No. NM_002852 using the above single-strand cDNA as a template, a full-length ORF gene was isolated. The fragment obtained through PCR was inserted to a vector by means of Zero Blunt TOPO PCR Cloning Kit, and nucleotide sequence was analyzed through a routine method. The vector was cut at KpnI site and BamHI site, to thereby obtain a fragment, and the fragment was inserted into a phCMV vector (product of Stratagene), whereby a transfer vector phCMV-PTX3 was produced.

Example 2

Construction of Cells Expressing Full-Length PTX3

According to the protocol FuGENE 6 (by Roche Molecular Biochemicals), CHO cells ($1\times10^5$ cells) were seeded on a 6-well dish on the day before transfection, and the cells were cultured overnight. Next day, the expression vector phCMV-PTX3 (8 μg) and FuGENE 6 reagent (16 μL) were added to a serum-free DMEM medium (100 μL), followed by incubation at room temperature for 20 minutes. The culture was added to the above cells. On the day after transfection, cloning was performed through the limiting dilution method employing G418 serving as a selection reagent. Culture supernatant of each clone was collected, and cells expressing PTX3 protein were screened. As a result, a clone constantly expressing PTX3 protein in an amount of about 2 to 3 μg/mL was selected. Hereinafter, the clone is represented by CHO-PTX3.

Example 3

Production of Recombinant PTX3 Protein

Purification of protein was performed in accordance with the method of Bottazzi et al. (Bottazzi B., Vouret-Craviari, et al., J. Biol. Chem. 1997; 272(52): 32817-23). Specifically, CHO-PTX3 was cultured in a 150-cm² flask and, subsequently, culturing was further performed for four days in roller bottles (product of BD Bioscience), each holding a serum-free medium (S-SFM-II, product of GIBCO/Invitrogen) (300 mL), while rotating speed was controlled to 1 rpm. The culture supernatants were collected, and the combined culture supernatant (1 L) was concentrated by means of an ultrafiltration membrane concentration apparatus, Pellicon XL device Biomax 100 (product of MILLIPORE) to 50 mL. The concentrate was dialyzed twice against 50 mM imidazole buffer (pH 6.6) (5 L). Subsequently, the dialyzed concentrate was subjected to ion-exchange chromatography employing HiPrep 16/10 Q XL (product of Pharmacia Biotech, Uppsala, Sweden). The eluate was washed until the background level was satisfactorily lowered. The NaCl concentration was increased from 0 to 0.58M over 35 minutes, and PTX3 was eluted with 1M NaCl. The eluate was monitored by absorbance at 280 nm. Fractions containing PTX3 protein were combined, the combined fraction was subjected to gel filtration chromatography employing Sephacryl S-300 and PBS serving as a developer. In order to selectively collect polymeric PTX3 from PTX3 species, the eluate was purified by means of Superose 6 column (product of GE Healthcare). Specifically, calibration was performed by use of a molecular weight standard, and PTX3 was applied to the column. Elution was performed with PBS at a flow rate of 0.4 mL/min. Eluated fractions were analyzed through SDS-PAGE, whereby purified recombinant polymeric PTX3 protein was obtained.

Example 4

Correspondence in Molecular Weight Between Recombinant PTX3 Protein and PTX3 in Clinical Sample The molecular weight of the recombinant PTX3 protein produced in Example 3 and that of PTX3 protein in a clinical sample were analyzed by use of individual fractions obtained through gel filtration by means of Superose 6 column (product of GE Healthcare). Specifically, after calibration by use of molecular weight standards, recombinant PTX3 protein was added to a human blood plasma sample having a PTX3 concentration lower than the measurement limit so as to adjust a protein concentration to 30 ng/mL. The sample was applied to the column and eluted by use of a buffer (20 mM HEPES, 15 mM NaCl, and 0.05% sodium azide, pH: 7.2) at a flow rate of 0.3 mL/min. Separately, a clinical sample (plasma), whose PTX3 concentration had been determined to be 10 ng/mL by ELISA, was subjected to gel filtration under the same conditions. The PTX3 level of each elution fraction was determined through ELISA.

As a result, both recombinant PTX3 protein and PTX3 in a clinical sample exhibited a peak in a fraction corresponding to about 900 kDa, as determined through calibration by use of molecular weight standards (FIG. 1).

Example 5

Production of Anti-PTX3 Monoclonal Antibody

The monoclonal antibody was produced through the following procedure. Specifically, Balb/C mice (CRL) or PTX3 knockout mice were immunized with PTX3. In priming, immunoprotein was prepared so that the dose was adjusted to 100 μg/mouse, and emulsified with FCA (Freund's complete adjuvant) (H37 Ra), Difco (3113-60), and Becton Dickinson (cat# 231131). The emulsion was subcutaneously injected. Two weeks after priming, immunoprotein was prepared so that the dose was adjusted to 50 μg/mouse, and emulsified with FIA (Freund's incomplete adjuvant), Difco (0639-60), and Becton Dickinson (cat# 263910). The emulsion was subcutaneously injected. Thereafter, a booster was administered twice with an interval of one week. In final immunization, immunoprotein was diluted with PBS so that the dose was adjusted to 50 μg/mouse, followed by administration to the tail vein. Through ELISA employing a PTX3-protein-coated immunoplate, saturation of the titer (in serum) of the antibody with respect to PTX3 was observed. Subsequently, mouse myeloma cells P3U1 and mouse spleen cells were fused by means of PEG 1500 (product of Roche Diagnostics, cat# 783641). The fused cells were seeded on a 96-well culture plate and, from the next day, selectively cultured in an HAT medium. The supernatant of the selected culture was screened through ELISA in the following manner. Specifically, the full-length PTX3 as described in Example 3 was immobilized, and a supernatant of hybridoma culture was added to the immobilized phase, followed by incubation. Screening was performed through the antigen-immobilized ELISA method including detection by means of a labeled anti-mouse antibody.

Positive clones were monoclonized through limiting dilution and cultured extensively to collect the culture supernatant. Screening through ELISA was performed on the basis of binding activity between an antibody and PTX3 protein. Thus, a number of anti-PTX3 antibodies exhibiting high binding performance were obtained.

The monoclonal antibodies were purified by use of Hi Trap Protein G HP (product of GE Healthcare). Specifically, a supernatant of hybridoma culture was directly applied to the above column and washed with a binding buffer (20 mM sodium phosphate (pH 7.0)), followed by elution with an eluting buffer (0.1M glycin-HCl (pH 2.7)). The eluate was introduced to a tube where a neutralizing buffer (1M Tris-HCl (pH 9.0)) had been placed for immediate neutralization. Antibody-eluted fractions were pooled and dialyzed against 0.05% Tween 20/PBS for one day (buffer substitution). The thus-purified antibodies were mixed with $NaN_3$ so as to adjust the antibody content to 0.02%, and stored at 4° C.

Example 6

Subclass of Anti-PTX3 Monoclonal Antibody

Isotyping of anti-PTX3 antibodies was performed by means of an ImmunoPure Monoclonal Antibody Isotyping Kit II (product of PIERCE, CAT# 37502) according to an instruction manual attached thereto. As a result, a large number of antibodies belonging to classes of IgG1, IgG2a, and IgM were obtained. Both PPMX 104 and PPMX 105 were classified to IgG1.

Example 7

Preparation of N-Terminal Polypeptide of PTX3 (N-PTX3)

An N-terminal polypeptide of PTX3 (N-PTX3) was expressed as a GST (glutathione-S-transferase) fusion protein by use of *E. coli* and purified. An N-PTX3-expression vector was constructed through a routine method. Specifically, a nucleotide sequence 1 to 522 was amplified through PCR by use of appropriate primers represented by SEQ ID NOs: 5 and 6 employing full-length PTX3 as a template. Subsequently, the expression vector was constructed by means of a pENTRTM/D-TOPO cloning kit Gateway (R) system and a pDESTTM24 vector (these items are products of Invitrogen) in accordance with the direction and dosage described in an instruction manual attached thereto.

*E. coli* BL21 Star™ (DE3) was transformed by the constructed vector, and a target gene was expressed through expression induction by use of arabinose. Subsequently, cells of *E. coli* which had been subjected to expression induction were collected and solubilized in a buffer containing a surfactant such as NP40 and lysozyme. The product was centrifuged, and a supernatant was collected and purified by means of a GST column. Specifically, a fusion protein was bound to GST Sepharose beads, and the beads were washed with PBS. Thereafter, the fusion protein was eluted with reduced-form glutathione solution. The thus-purified protein was subjected to SDS-PAGE, and purity, molecular weight, etc. were determined. The protein was employed as an antigen for antigen-immobilized ELISA.

Example 8

Epitope Analysis by use of N-Terminal Polypeptide of PTX3 (N-PTX3)

Binding sites of anti-PTX3 monoclonal antibodies (PPMX 0101, PPMX 0102, PPMX 0104, and PPMX 0105) to PTX3 protein were identified through the following procedure.

The full-length PTX3 protein (produced in Example 3) and the N-terminal polypeptide of PTX3 (N-PTX3) (described in Example 7) were employed as materials. Binding sites were identified through a generally employed antigen-immobilized ELISA. Specifically, the concentration of each of these proteins was adjusted to 5 µg/mL, and each sample was added to an ELISA plate at 100 µL/well. The sample was allowed to react overnight at 4° C. for immobilization. On the day after immobilization, the plate was washed thrice with a washing buffer (0.05% (v/v) Tween 20, PBS) (300 µL/well), followed by blocking through addition of TBS (10 mM Tris-HCl, 150 mM NaCl, pH: 7.5) containing 40% Block Ace (product of Dainippon Pharmaceutical Co., Ltd.) (150 µL). The plate was maintained at room temperature for several hours or overnight at 4° C., and a supernatant of hybridoma culture containing a monoclonal antibody or a diluted purified monoclonal antibody (100 µL/well) was added to the plate, followed by incubation at room temperature for two hours. Subsequently, peroxidase-labeled anti-mouse IgG goat IgG (product of Cappel) was 5,000-fold diluted with TBS (10 mM Tris-HCl, 150 mM NaCl, pH: 7.5) containing 10% Block Ace (product of Dainippon Pharmaceutical Co., Ltd.), and the diluted product (100 µL/well) was added to the plate, followed by incubation at room temperature for two hours. The plate was washed five times with a washing buffer (300 µL/well), and was allowed to develop color by use of TMB (product of Scytek, Cat#TM4999) in accordance with a protocol attached thereto. Absorbance was measured by means of a microplate reader.

Among monoclonal antibodies, those binding to full-length PTX3 protein and exhibiting high absorbance were analyzed in terms of recognition sites.

Example 9

Epitope Analysis Through Western Blotting by Use of Full-Length PTX3 Protein

The full-length recombinant PTX3 purified in Example 3 was treated with a sample buffer under reducing and non-reducing conditions, respectively. Each sample was applied to a gel plate at 60 ng/lane and SDS-PAGE was performed. The sample was electrotransferred to a Hybond-ECL membrane (product of GE Healthcare) at 38V over 16 hours, followed by blocking with Block Ace (Snow brand Milk Products) at room temperature for one hour. Subsequently, an anti-PTX3 antibody (0.3 µg) was incorporated into 40% Block Ace (Snow brand Milk Products)/TBS solution, and the antibody solution was reacted with the sample at room temperature for one hour. The membrane was washed (5 min×3) with TBST (50 mM Tris-HCl (pH: 7.5), 150 mM NaCl, 0.05% Tween 20). Subsequently, a solution of HRP-labeled IgG antibody (product of GE Healthcare) diluted to 5,000-fold with 10% Block Ace (Snow brand Milk Products)/TBS was added thereto, followed by reaction at room temperature for one hour. The membrane was washed thrice with TBST. Finally, an ECL-detecting reagent (product of GE Healthcare) was applied, and an X-ray film was sensitized by resultant chemoluminescence signals over five minutes.

Figure 2:
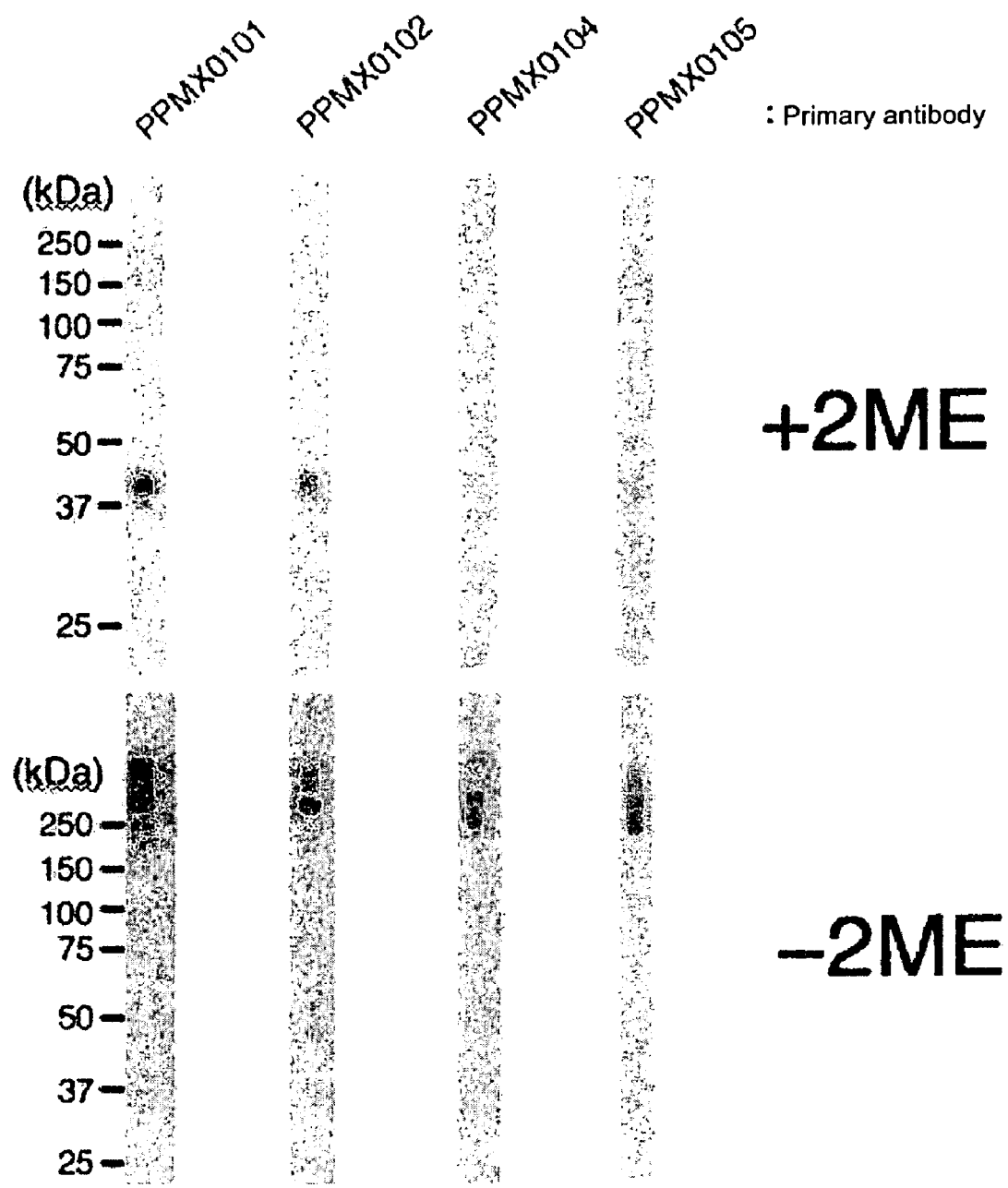
[FIG. 2] Reactivity of anti-PTX3 monoclonal antibodies with full-length PTX3 in Western blotting under reducing/non-reducing conditions.

Under reducing condition, PPMX 0101 and PPMX 0102 were reacted with full-length PTX3, while PPMX 0104 and PPMX 0105 exhibited no reactivity. Under non-reducing conditions, all antibodies reacted with full-length PTX3 (FIG. 2).

Example 10

Preparation of C-Terminal Polypeptide of PTX3 (C-PTX3)

A C-terminal polypeptide of PTX3 (C-PTX3) (a sequence from 179 to 381 in SEQ ID NO: 2) was forcedly expressed in CHO cells through the following procedure. Separately, an N-terminal polypeptide encoding a sequence from 1 to 151 in SEQ ID NO: 2 (N-PTX3 (2)), which differs from the N-terminal polypeptide of PTX3 (N-PTX3) prepared in Example 7, was also prepared.

Firstly, by use of the human PTX3 cloned in Example 1 as a template, cDNA encoding amino acid residues 179 to 381 of PTX3 was amplified through PCR, and the product was inserted to the BamHI site of pSG5 vector (product of Stratagene), to thereby construct an expression vector. When preparing the cDNA, the primer was synthesized so that a PTX3 signal peptide was attached to the 3'-terminal thereof, and PCR amplification was performed.

A partial-length PTX3 protein was forcedly expressed in CHO cells through the following procedure. Specifically, CHO cells ($0.8 \times 10^6$) were seeded on a 10-cm dish, and on the day after seeding, the cells were transfected with plasmid DNA (8 µg) by use of a FuGENE 6 Transfection Reagent (product of Roche).

Forty-eight hours after transfection, cells were recovered by means of a cell-scraper, and RIPA buffer (10 mM Tris-Cl, 150 mM NaCl, 5 mM EDTA, 1% Triton X-100, 1% deoxycholate, 0.1% SDS, pH: 7.4) (200 µL) was added to the recovered cells. The cells were lysed by placing them on ice for 15 minutes. Subsequently, the product was centrifuged at 15,000×g and 4° C. for 15 minutes, and the supernatant was collected and employed as an expressed protein solution.

The N-terminal polypeptide encoding an amino acid sequence 1 to 151 in SEQ ID NO: 2 (N-PTX3 (2)), which differs from the N-terminal polypeptide of PTX3 (N-PTX3) prepared in Example 7, was prepared through the same procedure as employed in preparation of C-PTX3. Thus, a partial-length (sequence: 1 to 151) PTX3 polypeptide was obtained. In this case, however, since the N-terminal region had a signal polypeptide in a sequence of 1 to 17, addition of a signal peptide was not performed.

Figure 3:
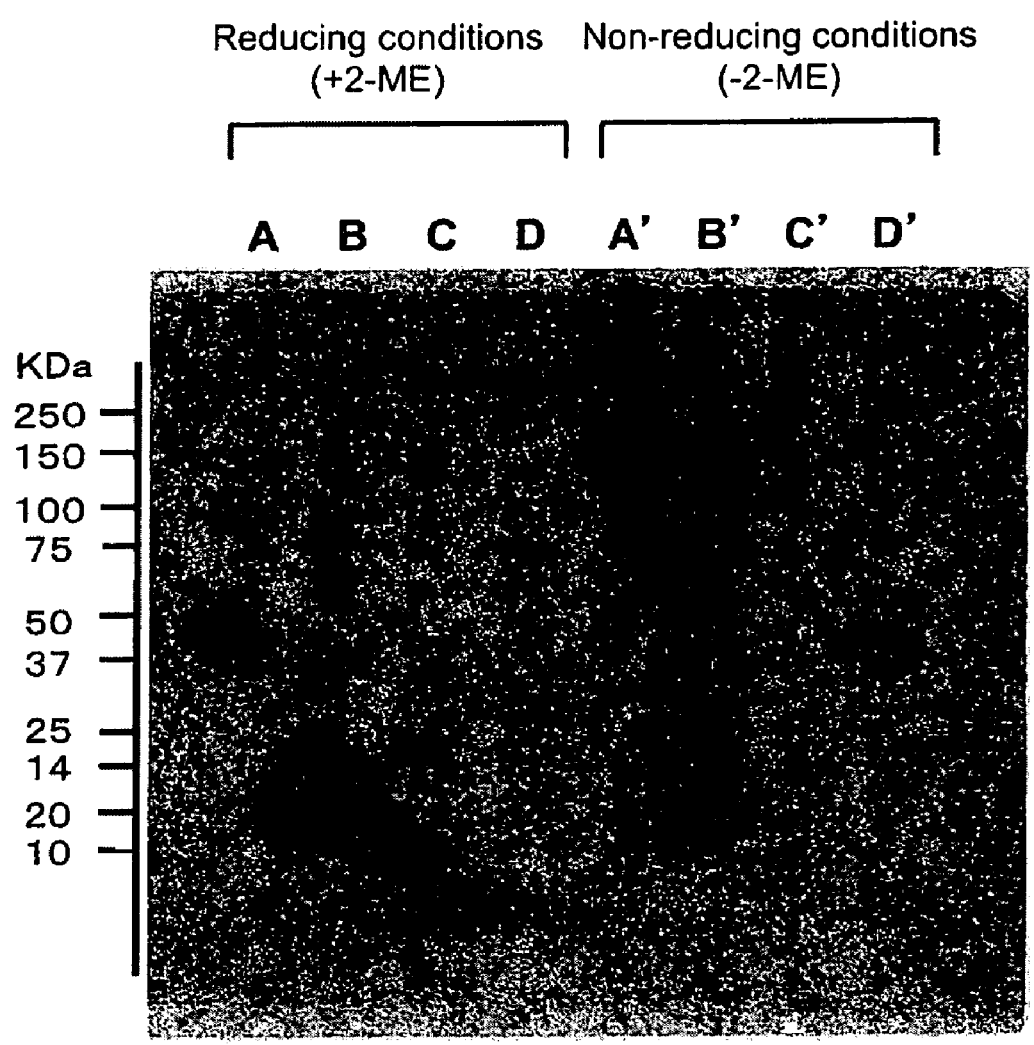
[FIG. 3] Results of Western blotting in Example 11 employing a PTX3 polypeptide expression product as a sample and blood serum from PTX3-sensitized mouse as a primary antibody. A and A' represent samples of full-length PTX3 treated under reducing and non-reducing conditions, respectively; B and B' represent samples of N-terminal polypeptide of PTX3 (N-PTX3 (2)) treated under reducing and non-reducing conditions, respectively; C and C' represent samples of C-terminal polypeptide of PTX3 (C-PTX3) treated under reducing and non-reducing conditions, respectively; and D and D' represent samples of a lysate of a supernatant of CHO cell culture to which no gene had been transferred and which had been treated under reducing and non-reducing conditions, respectively (negative controls).
Figure 4:
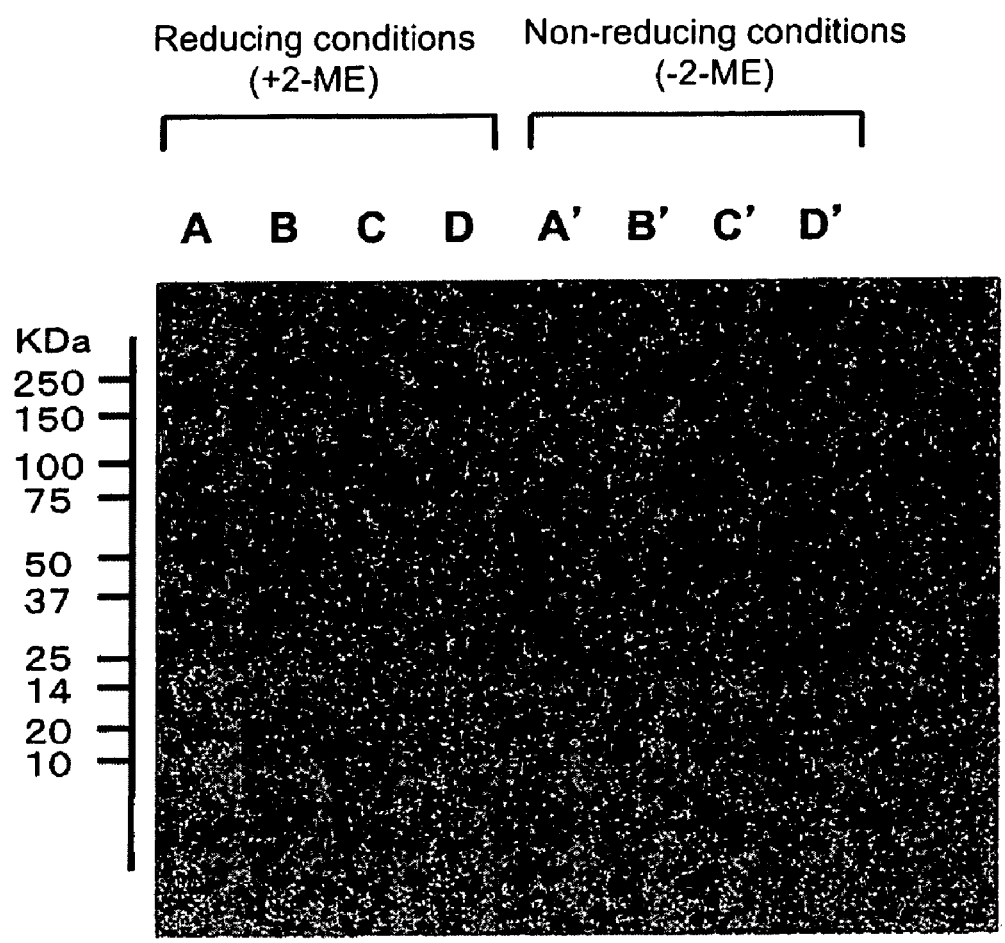
[FIG. 4] Results of Western blotting in Example 11 employing a culture supernatant of hybridoma Hyb-3423 producing an anti-HBs antibody. A and A' represent samples of full-length PTX3 treated under reducing conditions and non-reducing conditions, respectively; B and B' represent samples of N-terminal polypeptide of PTX3 (N-PTX3 (2)) treated under reducing and non-reducing conditions, respectively; C and C' represent samples of C-terminal polypeptide of PTX3 (C-PTX3) treated under reducing and non-reducing conditions, respectively; and D and D' represent: samples of a lysate of a supernatant of CHO cell culture to which no gene had been transferred and which had been treated under reducing and non-reducing conditions, respectively (negative controls).

Next, identification of the expressed product was performed. The expressed protein was treated with a sample buffer under reducing conditions (with adding 2-ME) or non-reducing conditions (without adding 2-ME). Each expressed protein solution was applied to a gel plate at 20 ng/lane and SDS-PAGE (polyacrylamide gel electrophoresis) was performed. The sample was electrotransferred to a Hybond-P (product of GE Healthcare), followed by blocking through immersion of the membrane in 100% Block Ace (Snow brand Milk Products) at room temperature for one hour with shaking. Subsequently, a blood serum which had been obtained from a mouse sensitized by full-length PTX3 was suspended in 40% Block Ace/TBS (10 mM Tris-Cl, 150 mM NaCl, pH: 7.5). The membrane was immersed in the suspension at room temperature for one hour with shaking, to thereby perform a primary reaction. After the primary reaction, the membrane was washed twice (5 min) with TBST (TBS+0.1% Tween 20), and immersed in a solution of HRP-labeled anti-mouse IgG (product of GE Healthcare, cat. NA931) diluted to 5,000-fold with 10% Block Ace/TBS, at room temperature for one hour with shaking, to thereby perform a secondary reaction. After the secondary reaction, the membrane was washed thrice (5 min) with TBST (TBS+0.1% Tween 20), and was allowed to develop color by use of ECL (product of GE Healthcare) (FIG. 3). A negative control was also subjected to western blotting, employing, a culture supernatant of Hyb-3423 producing a monoclonal antibody to type-B hepatitis virus S antigen (HBs antigen) not recognizing PTX3 (primary antibody), and an anti-mouse IgG antibody (product of GE Healthcare) as a secondary antibody (FIG. 4).

Example 11

Epitope Analysis by Use of C-Terminal Polypeptide of PTX3 (C-PTX3)

A lysate of CHO cells expressing the N-terminal polypeptide (N-PTX3 (2)) and C-terminal polypeptide (C-PTX3), prepared in Example 9, a lysate of CHO cells to which no gene had been transferred, and purified full-length recombinant PTX3 were treated with a sample buffer under reducing conditions (with adding 2-ME) and non-reducing conditions (w/o adding 2-ME), respectively. Each lysate was applied to a gel plate at 20 µg/lane, and full-length PTX3 was applied at 3 ng/lane. Western blotting was performed by use of PPMX 0104 as a primary antibody in accordance with the method as described in Example 9.

Figure 5:
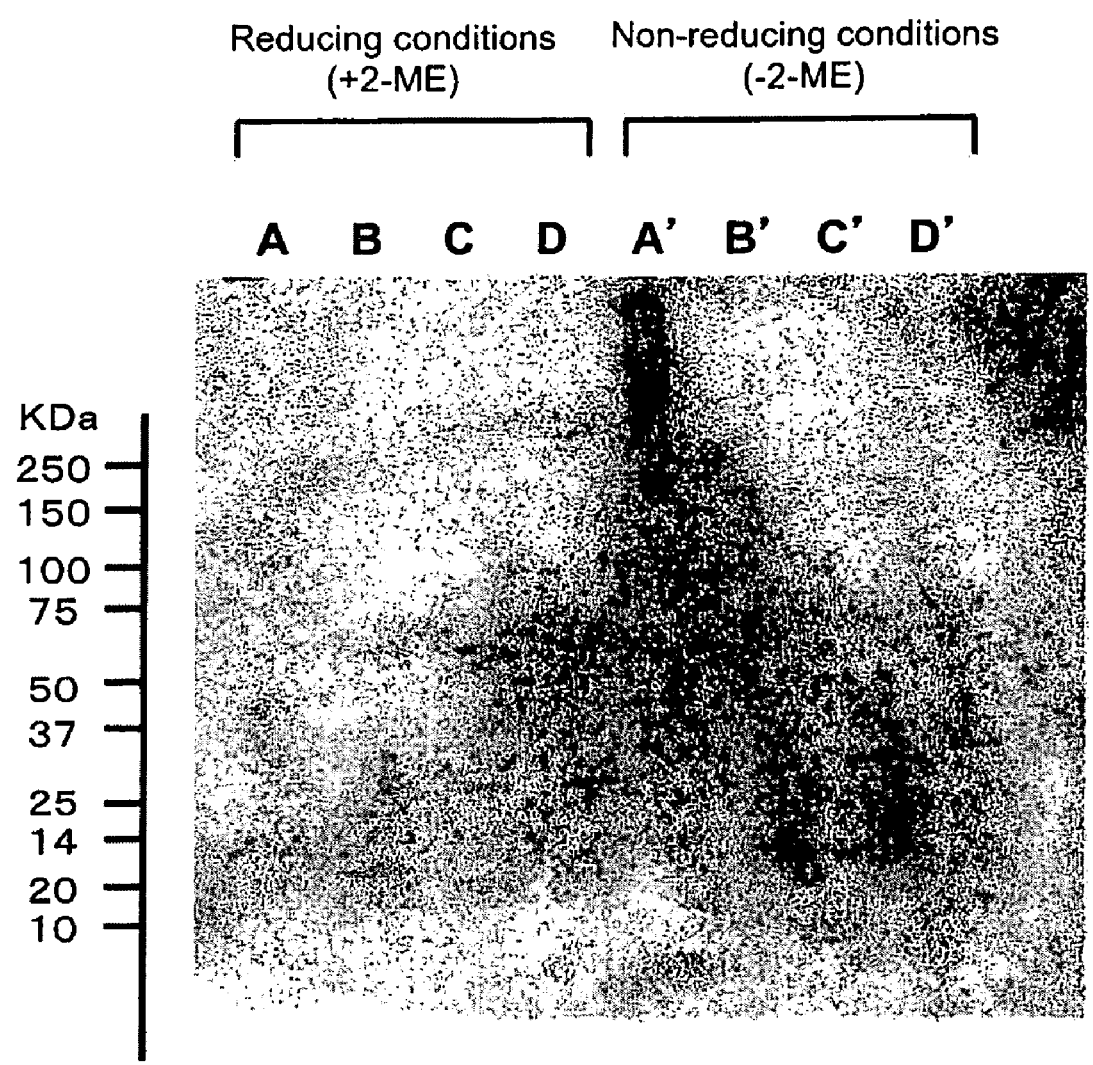
[FIG. 5] Results of Western blotting in Example 11 employing an anti-PTX3 monoclonal antibody PPMX 0104. A and A' represent samples of full-length PTX3 treated under reducing conditions and non-reducing conditions, respectively; B and B' represent samples of N-terminal polypeptide of PTX3 (N-PTX3 (2)) treated under reducing and non-reducing conditions, respectively; C and C' represent samples of C-terminal polypeptide of PTX3 (C-PTX3) treated under reducing and non-reducing conditions, respectively; and D and D' represent: samples of a lysate of a supernatant of CHO cell culture to which no gene had been transferred and which had been treated under reducing and non-reducing conditions, respectively (negative controls).

As a result, under reducing conditions, PPMX 0104 did not recognize full-length PTX3, the N-terminal polypeptide (N-PTX3 (2)), or the C-terminal polypeptide (C-PTX3). Under non-reducing conditions, PPMX 0104 reacted only with full-length PTX3 (FIG. 5).

Example 12

Reactivity of Monoclonal Antibodies to a Protease-Digested Product of Full-Length PTX3 Protein Under Reducing Conditions The binding sites of the antibodies to PTX3 protein were more precisely identified. Specifically, PTX3 was fragmented through enzymatic digestion, and the fragments were recovered through reverse phase HPLC. The reactivity of the monoclonal antibodies to the thus-recovered peptides was investigated through ELISA.

Figure 6:
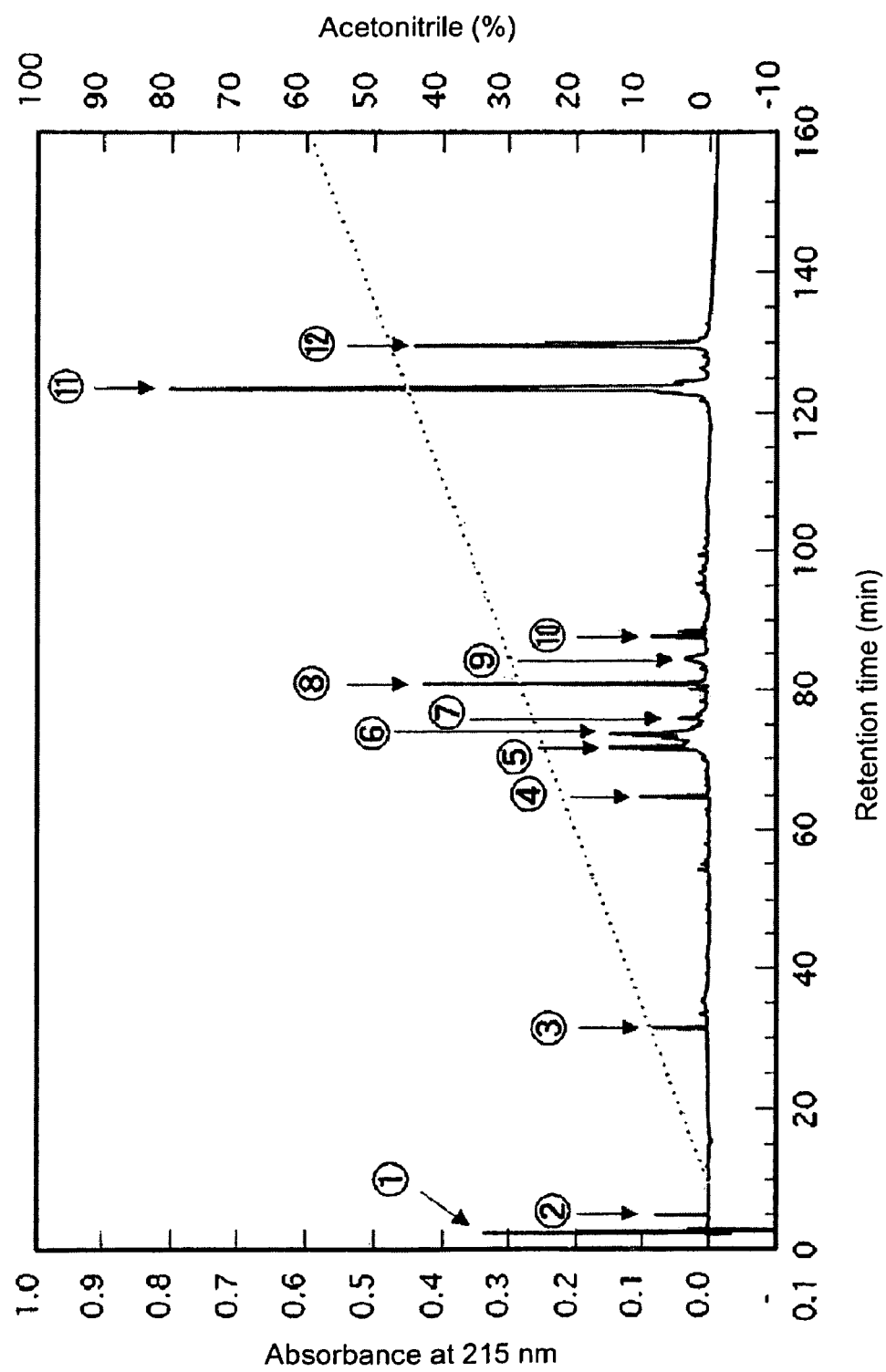
[FIG. 6] Results from reverse phase HPLC separation (Example 12) of full-length PTX3 digested products.

Firstly, PTX3 protein was dissolved in a mixture of 0.5M Tris-HCl, 6M guanidine-HCl, and 10 mM EDTA, (pH: 8.5), and DDT (315-fold amount by mole with respect to PTX3) was added to the solution. The mixture was allowed to stand at 37° C. for two hours, to thereby perform reducing treatment. Subsequently, 4-vinylpyridine (3.1-fold amount by mole with respect to DTT) was further added thereto, and the reaction product was allowed to stand at room temperature for two hours in the dark, to thereby perform pyridylethylation of an SH group. The product was sequentially dialyzed against pure water and a mixture of 50 mM Tris-HCl and 3M urea (pH: 9.0). Lysyl endopeptidase (product of Wako Pure Chemicals Industries, Ltd.) was added to the dialyzed product in a 1/50 amount by mole with respect to PTX3, and the mixture was allowed to react at 37° C. for 18 hours, to thereby enzymatically digest PTX3 protein. The enzyme-digested product was applied to a Symmetry 300 C18 column (product of Waters), and eluted with acetonitrile (gradient: 0 to 60%) over 150 min (flow rate: 0.8 mL/min). The eluted fragments were recovered (FIG. 6). These fragment solution were 50-fold diluted with PBS and each sample was added to an ELISA plate at 100 µL/well, and the sample was allowed to react overnight at 4° C. for immobilization. ELISA was performed through the following procedure. Specifically, after immobilization, the plate was washed with thrice with a washing buffer (0.05% (v/v) Tween 20, PBS) (300 µL/well), followed by blocking through addition of TBS (10 mM Tris-HCl, 150 mM NaCl, pH: 7.5) containing 40% Block Ace (product of Dainippon Pharmaceutical Co., Ltd.) (150 µL). The plate was maintained at room temperature for several hours or overnight at 4° C. PPMX 0104 antibody or PPMX 0105 antibody was dissolved in the solution identical to the blocking solution to a final concentration of 10 μg/mL. Each solution (100 μL/well) was added to the plate, followed by incubation at room temperature for two hours. Subsequently, peroxidase-labeled anti-mouse IgG goat IgG (product of Cappel) was 5,000-fold diluted with TBS (10 mM Tris-HCl, 150 mM NaCl, pH: 7.5) containing 10% Block Ace (product of Dainippon Pharmaceutical Co., Ltd.), and the diluted product (100 μL/well) was added to the plate, followed by incubation at room temperature for two hours. The plate was washed five times with a washing buffer (300 μL/well), and was allowed to develop color by use of TMB (product of Scytek, Cat#TM4999) in accordance with a protocol attached thereto. Absorbance was measured by means of a microplate reader.

Figure 7:
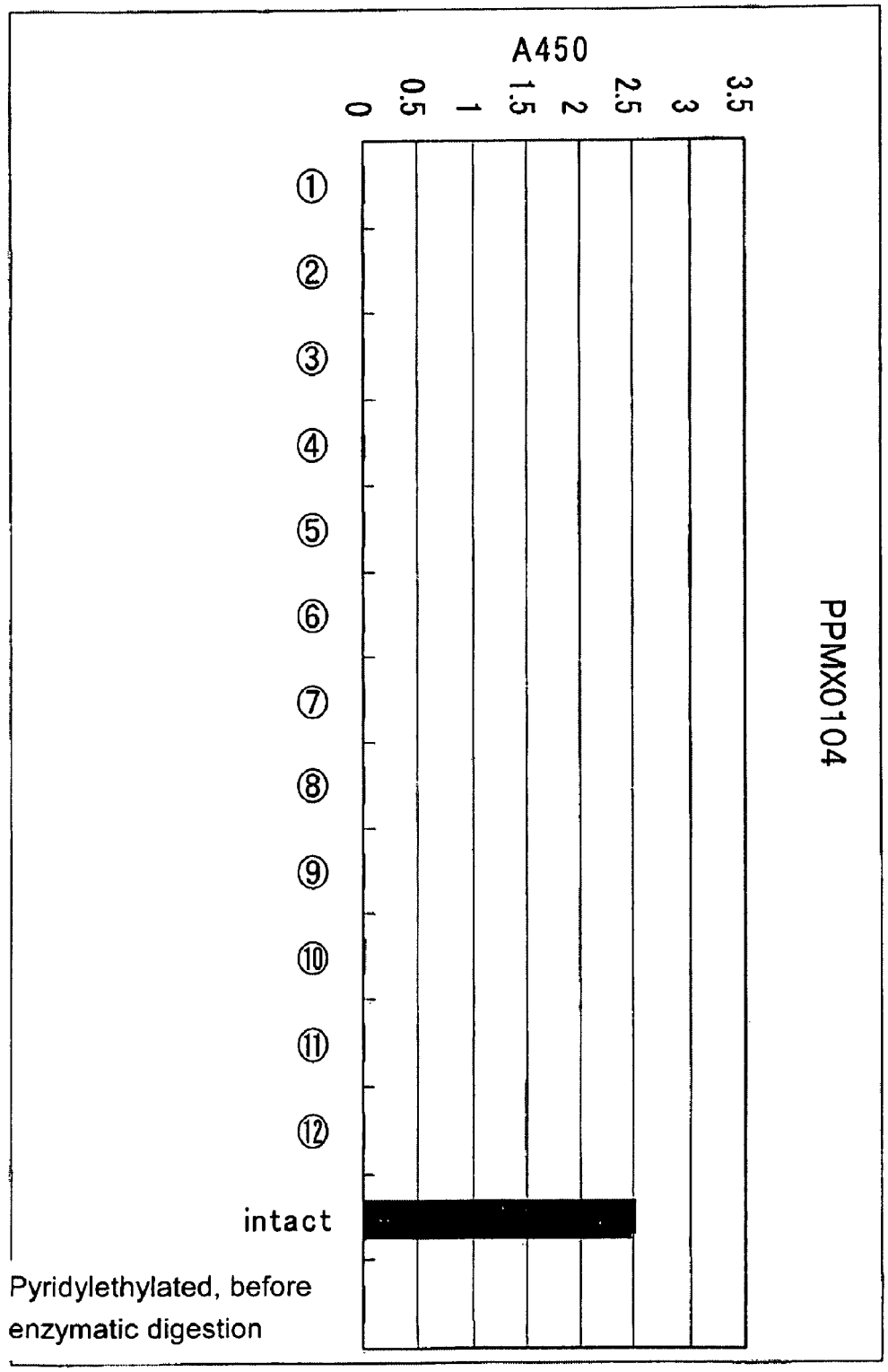
[FIG. 7] Results of ELISA performed in Example 12, showing to reactivity of PPMX 0104 with lysyl endopeptidase-digested products of full-length PTX3 which has undergone reducing treatment.
Figure 8:
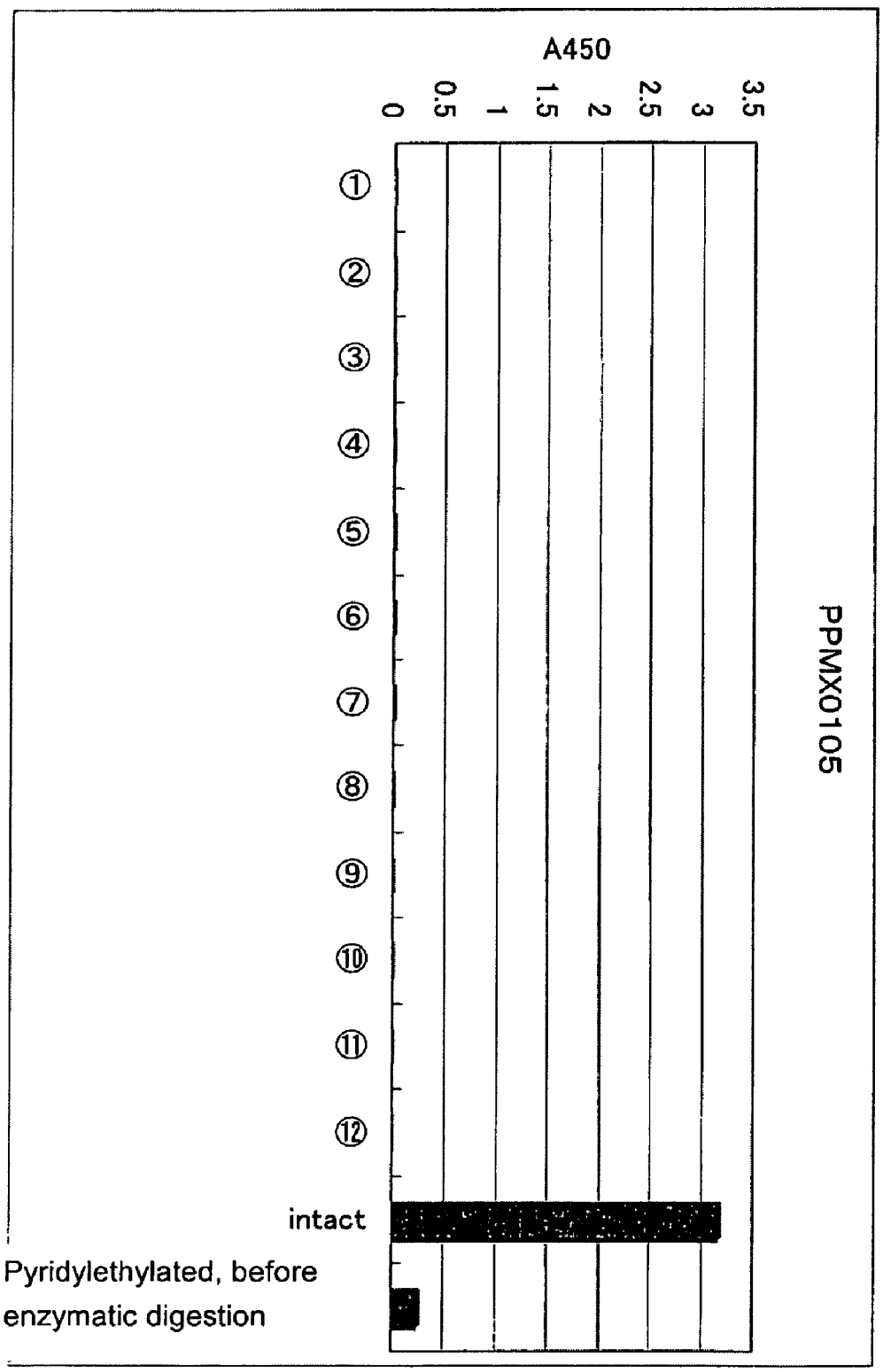
[FIG. 8] Results of ELISA in performed in Example 12, showing to reactivity of PPMX 0105 with lysyl endopeptidase-digested products of full-length PTX3 which has undergone reducing treatment.

As a result, these antibodies did not react with enzymatically cleaved peptides (FIGS. 7 and 8). Therefore, PPMX 0104 and PPMX 0105 were thought to be an antibody recognizing a conformational structure of PTX3. Also, PPMX 0104 and PPMX 0105 exhibited no substantial reactivity with PTX3 before enzyme-digestion; i.e., PTX3 which had undergone reduction and pyridylethylation. The fact also supported that these antibodies recognize a conformational structure of PTX3 having an S—S bond.

Example 13

Figure 9:
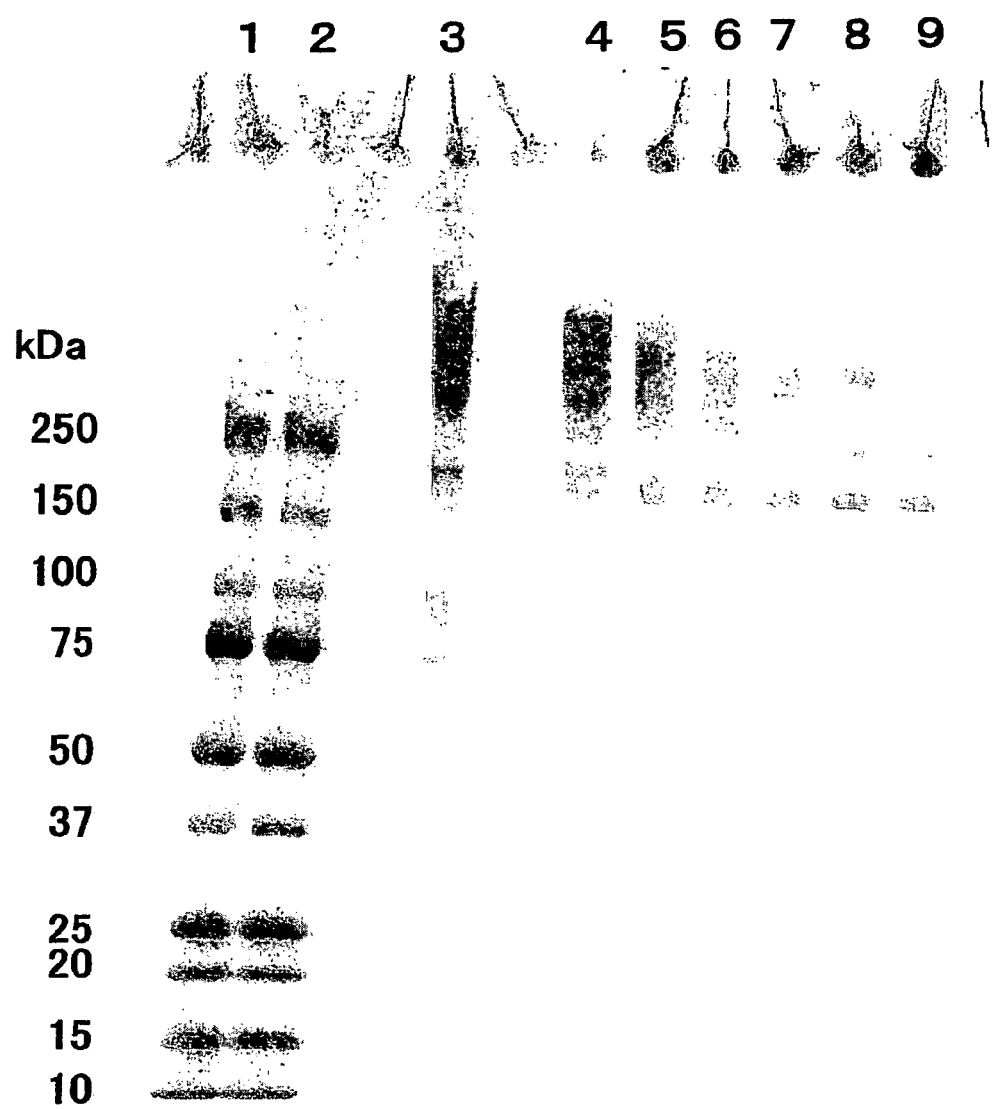
[FIG. 9] Results of Coomassie brilliant blue staining performed in Example 13. Full-length PTX3 has been digested by lysyl endopeptidase under non-reducing conditions, and the digested products have been subjected to SDS-PAGE (1: molecular weight marker, 2: molecular weight marker, 3: undigested full-length PTX3, 4: 0 hour after digestion, 5: 0.5 hours after digestion, 6: 1 hour after digestion, 7: 2 hours after digestion, 8: 4 hours after digestion, and 9: 8 hours after digestion).

Reactivity of Monoclonal Antibodies to a Lysyl Endopeptidase-Digested Product of Full-Length PTX3 Protein Under Non-Reducing Conditions The full-length PTX3 protein produced in Example 3 was digested by use of lysyl endopeptidase (product of Wako Pure Chemicals Industries, Ltd.) at 30° C. in 200 mM Tris-HCl buffer for a digestion time of 0, 0.5, 1, 2, 4, and 8 hours. After passage of a predetermined digestion time, digestion was terminated through addition of DFP (diisopropyl fluorophosphate), and the digestion sample was fractionated through SDS-PAGE. Through staining the gel with Coomassie brilliant blue (CBB), breakage of PTX3 was observed (FIG. 9).

Figure 10:
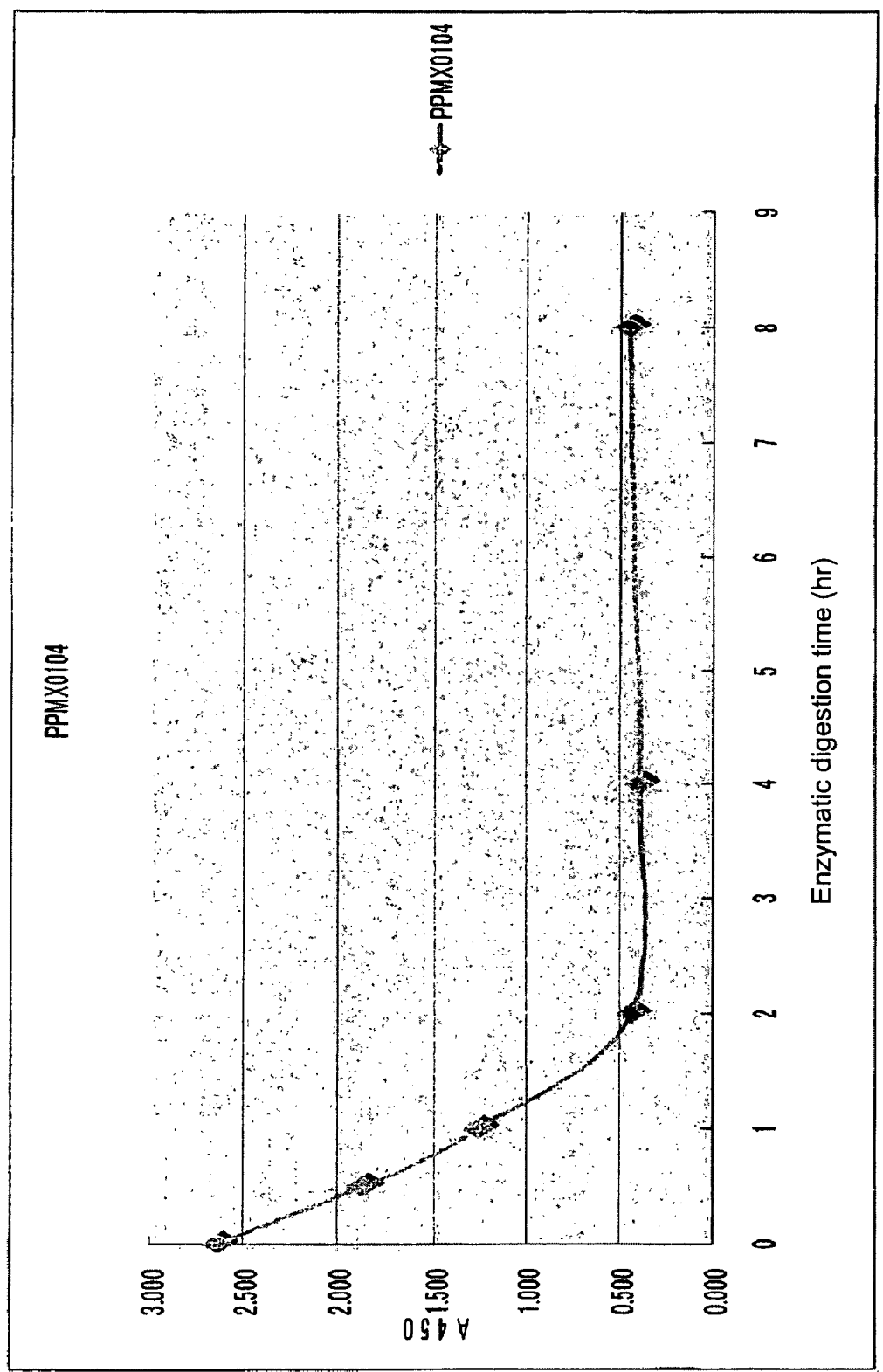
[FIG. 10] Relationship between digestion time of full-length PTX3 with lysyl endopeptidase under non-reducing conditions (Example 13) and the reactivity of the digested product to PPMX 0104.
Figure 11:
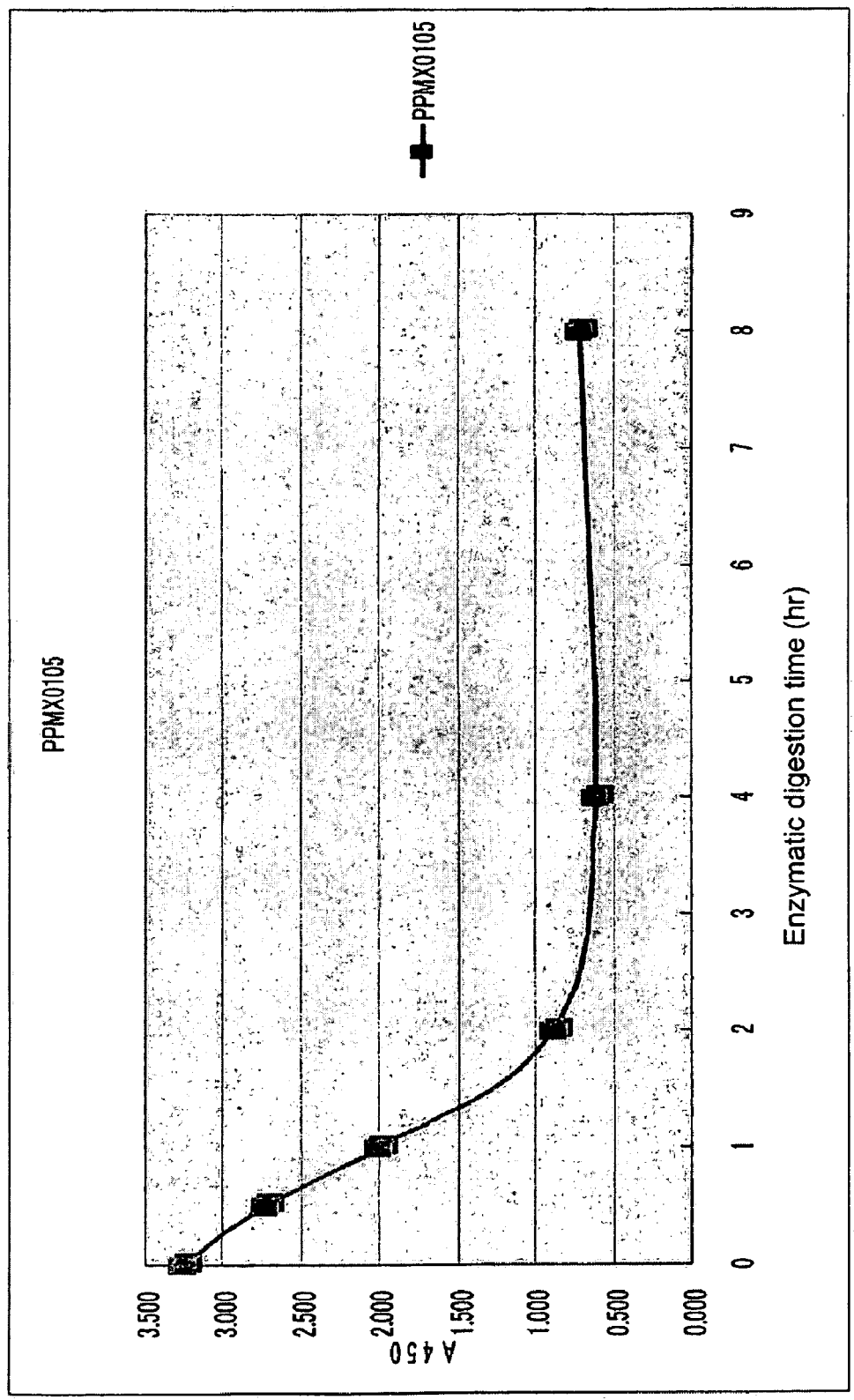
[FIG. 11] Relationship between digestion time of full-length PTX3 with lysyl endopeptidase under non-reducing condition (Example 13) and the reactivity of the digested product to PPMX 0105.

Reactivity of anti-PTX3 monoclonal antibodies, PPMX 0104 and PPMX 0105, to a lysyl endopeptidase-digested sample was investigated through generally employed immobilized phase ELISA. Specifically, in the ELISA procedure, a sample which had undergone digestion with lysyl endopeptidase was immobilized on an ELISA plate, and PPMX 0104 or PPMX 0105 serving as a primary antibody was reacted with the sample. A horseradish peroxidase-labeled anti-mouse Ig goat antibody (product of GE Healthcare) was employed as a secondary antibody. The relationships between lysyl endopeptidase PTX3 digestion time and ELISA measurements are shown in FIGS. 10 and 11.

On the basis of the experiment, hybridomas of PPMX 0104 and PPMX 0105, which produce monoclonal antibodies recognizing a conformational structure of PTX3, were deposited as FERM BP-10719 and FERM BP-10720, respectively, to National Institute of Advanced Industrial Science and technology, International Patent Organism Depositary (Central 6th, 1-1-1 Higashi, Tsukuba City, Ibaraki, 305-8566, Japan) (deposited on Sep. 22, 2005).

Example 14

Determination of Dissociation Constant of PTX3 Monoclonal Antibodies

Binding constant was determined by means of a BIAcore 3000 system (product of BIAcore, Uppsala, Sweden). Firstly, an anti-mouse IgG antibody was immobilized on a sensor chip CM5 through NHS/EDC coupling. Then, a suspension (10 μg/mL) of an anti-PTX3 antibody (PPMX 0104 or PPMX 0105) in HBS-EP buffer (10 mM HEPES (pH: 7.4), 150 mM NaCl, 3 mM EDTA, 0.005% surfactant P20) was injected to the sensor, whereby the antibody was immobilized in an amount of several hundreds of RU. Subsequently, a suspension of recombinant PTX3 in HBS-EP buffer was injected. Binding and dissociation were detected, and dissociation constant was determined by means of an analysis program (BIA evaluation).

As a result, both PPMX 0104 and PPMX 0105, produced in the experiment, exhibited low dissociation constant. Particularly, PPMX 0104 exhibited the lowest dissociation constant, indicating high affinity to PTX3 (Table 1).

TABLE 1

| Dissociation constant of anti-PTX3 antibodies | |
|---|---|
| Antibody | KD |
| PPMX 0104 | $1.23 \times 10^{-10}$ |
| PPMX 0105 | $6.17 \times 10^{-10}$ |

Example 15

Cross-Reactivity Between Anti-PTX3 Monoclonal Antibody and SAP or CRP

Cross-reaction between PPMX 0104 or PPMX 0105 and SAP or CRP was investigated through generally employed antigen-immobilized ELISA. Specifically, 5 μg/mL solutions of full-length PTX3 protein, human CRP (product of Nippon Biotest Labo.), and human SAP (product of Wako Pure Chemicals Industries, Ltd.) were prepared. Each solution was added to an ELISA plate at 100 μL/well. The sample was allowed to react overnight at 4° C. for immobilization. On the day after immobilization, the plate was washed with thrice with a washing buffer (0.05% (v/v) Tween 20, PBS) (300 μL/well), followed by blocking through addition of TBS (10 mM Tris-HCl, 150 mM NaCl, pH: 7.5) containing 40% Block Ace (product of Dainippon Pharmaceutical Co., Ltd.) (150 μL). The plate was maintained at room temperature for several hours or overnight at 4° C., and a supernatant of hybridoma culture containing a monoclonal antibody or a diluted purified monoclonal antibody (100 μL/well) was added to the plate, followed by incubation at room temperature for two hours. Subsequently, peroxidase-labeled anti-mouse IgG goat IgG (product of Cappel) was 5,000-fold diluted with TBS (10 mM Tris-HCl, 150 mM NaCl, pH: 7.5) containing 10% Block Ace (product of Dainippon Pharmaceutical Co., Ltd.), and the diluted product (100 μL/well) was added to the plate, followed by incubation at room temperature for two hours. The plate was washed five times with a washing buffer (300 μL/well), and was allowed to develop color by use of TMB (product of Scytek, Cat#TM4999) in accordance with a protocol attached thereto. Absorbance was measured by means of a microplate reader.

The monoclonal antibodies, PPMX 0104 and PPMX 0105, were strongly reacted with full-length PTX3, but were not reacted with SAP or CRP (Table 2).

TABLE 2

Reactivity of PPMX 0104 and PPMX 0105 to PTX3, CRP, or SAP

| Antibody | Absorbance (450 nm) | | |
|---|---|---|---|
| | PTX3 | CRP | SAP |
| PPMX 0104 | 2.350 | 0.012 | 0.007 |
| PPMX 0105 | 2.263 | 0.007 | 0.004 |

Example 16

Formation of F(ab')$_2$ of the Antibody

F(ab')$_2$ of the antibody was formed through the following procedure. The antibody purified through the monoclonal antibody production method as described in Example 4 was dialyzed against a dilute buffer (5 mM Tris-HCl and 150 mM NaCl, pH: 7.5). An antibody of subclass IgG1 was 2-fold diluted with pepsin digestion buffer (0.2M sodium citrate buffer) (pH: 3.7), and an antibody of subclass IgG2a was similarly diluted with the same buffer (pH: 4.0), and the samples were heated at 37° C. for five minutes. Subsequently, 10-mg/mL and 1-mg/mL pepsin solutions were prepared by use of the pepsin digestion buffer (pH: 4.0), and each pepsin solution was added to a heated IgG1 sample in an amount of 130:1 (antibody:pepsin, by mass), and to a heated IgG2a sample in an amount of 8:1 (antibody:pepsin, by mass), followed by incubation at 37° C. for 2.5 hours. Digestion reaction was terminated through addition of a 1/10 volume of 2M Tris.

Example 17

Labeling of Antibodies

Generally, direct labeling of antibodies is performed by binding an enzyme such as alkaline phosphatase or peroxidase to an amino group or an SH group through the periodic acid method, the maleimide method, etc. In this experiment, each of the antibodies produced in Example 12 was labeled with peroxidase at SH groups thereof through the maleimide method by means of a peroxidase labeling kit-SH (product of Dojindo Laboratories) in accordance with the direction and dosage described in an instruction manual attached thereto.

Example 18

Construction of ELISA System and Determination Employing the System

In order to detect PTX3 in blood, a sandwich ELISA system for PTX3 was constructed in the following manner. Specifically, an antibody (F(ab')$_2$ of PPMX 0104) (5 µg/mL) was applied to a 96-well plate (100 µL/well), and incubated overnight at 4° C., to thereby immobilize the antibody to the plate.

The next day, the plate was washed three times with a washing buffer (0.05% (v/v) Tween 20, PBS) (300 µL/well), and blocked with an immunoassay stabilizer (product of ABI, ABI #10-601-001) (150 µL). Several hours after maintaining at room temperature, or after overnight storage at 4° C., purified protein, human serum, etc. which had been appropriately diluted with a diluting buffer (50 mM Tris-Cl pH 8.0, 0.15M NaCl) containing animal serum or other components was added to the plate, followed by incubation at room temperature for two hours. Subsequently, an HRPO (horseradish peroxidase)-labeled Fab' of PPMX 0105 antibody which had been diluted to 20 µg/mL with PBS(−) containing an animal serum or other components was added to the plate, followed by incubation at room temperature for two hours. After removal of reaction solution, the plate was washed five times with a washing buffer (300 µL/well), and samples were allowed to develop color by use of TMB (product of Scytek, Cat# TM4999) in accordance with the attached protocol. The absorbance was measured by means of a microplate reader. The PTX3 protein level of each sample was calculated from the absorbance value through spreadsheet calculation software, GraphPad PRISM (product of GraphPad software Inc., ver. 3.0).

Example 19

Comparison of the Assay System of the Invention with a Conventional Assay System in Terms of Standard Curve A standard curve employed in ELISA was made by use of serial dilution solutions of a standard product (concentrations: 3, 1.1, 0.37, 0.12, 0.041, 0.014, 0.005 ng/mL), the standard product being concentration-verified PTX3 protein (product of ALEXIS). In order to compare sensitivity in ELISA, a similar standard curve was made in a similar manner by use of a kit used in WO 2005/080981 for assaying blood level of the protein in patients.

Figure 12:
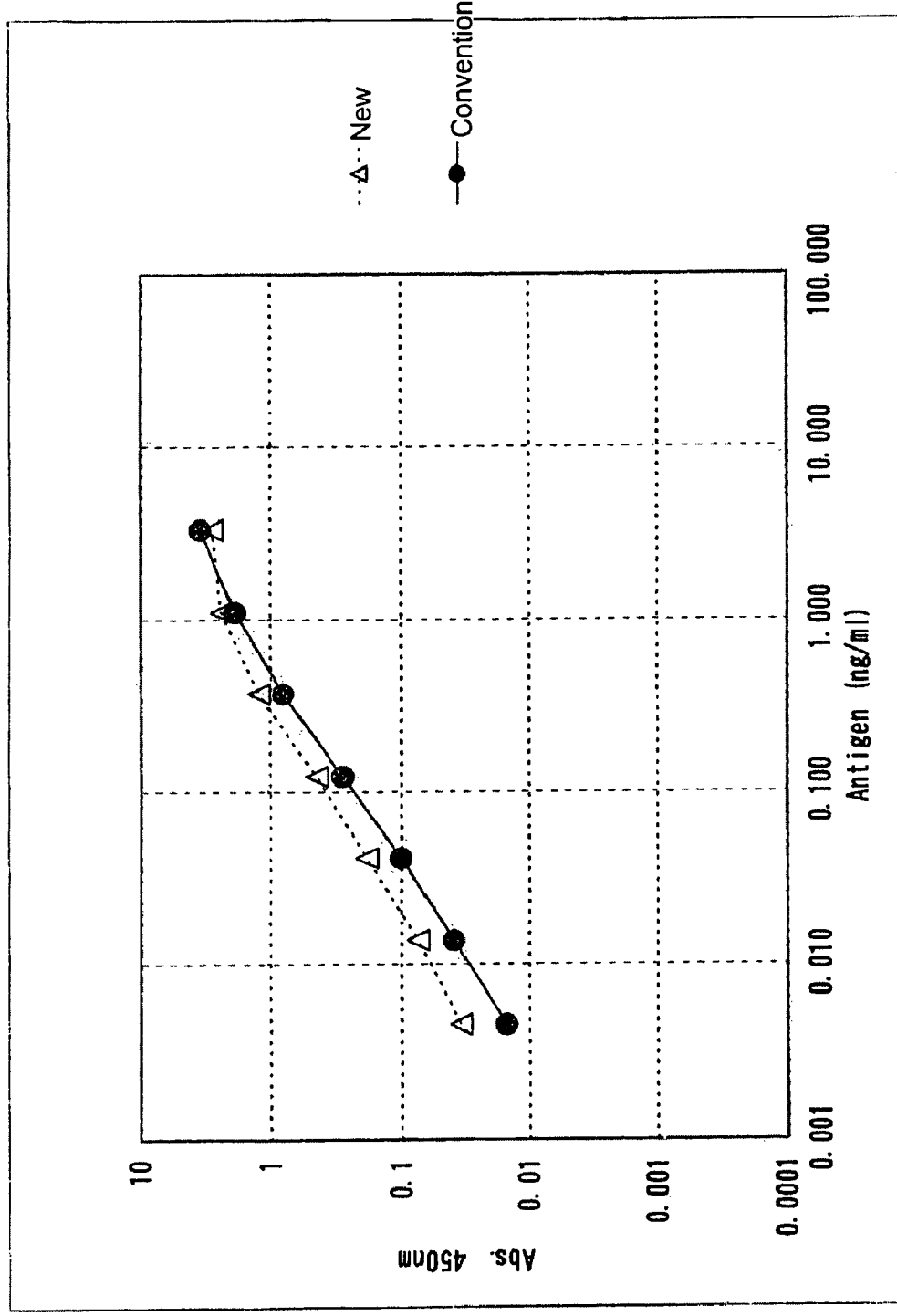
[FIG. 12] Comparison of standard curve between a conventional ELISA kit and the ELISA kit of the invention.

Through comparison of a plurality of assay systems produced in the present invention with an assay disclosed in WO 2005/080981 by use of an antibody, a remarkably higher sensitivity was observed in a new assay system; e.g., a kit employing PPMX 0104 as a pre-coating antibody and PPMX 0105 as a labeled antibody (FIG. 12).

Notably, while the recognition site of the antibody employed in the conventional assay system is an N-terminal region of a PTX3 molecule, PPMX 0104 and PPMX 0105 employed in the new assay kit were found to be an antibody recognizing a conformational epitope of PTX3.

Example 20

Comparison of the Assay System of the Present Invention with the Conventional Assay System (Addition-Recovery Test and Reproducibility Test)

In order to compare the new assay system with a conventional one in terms of ELISA sensitivity as described above, an addition-recovery test and a reproducibility test were performed by use of a kit disclosed in WO 2005/080981 for blood level assay of patients, whereby comparative data were obtained in parallel. Actually, samples employed in the addition-recovery test were prepared in the following manner. Specifically, reference samples were prepared by adding an antigen to a sample dilution buffer so as to attain a final concentration of 2, 5, and 10 ng/mL. Test samples were prepared by adding the same antigen at the same concentrations to eight human blood plasma samples. In the reproducibility test, plasma samples obtained from six healthy people and those obtained from three unstable angina patients were employed, and measurement was performed in accordance with the following procedure. Specifically, each prepared sample (10 µL) was injected to wells where a sample dilution buffer (100 µL/well) had been injected, and reacted with shaking at room temperature for one hour. Subsequently, the plate was washed five times with a washing solution (PBS, 0.05% Tween 20), and a labeled antibody solution (100 µL)

was injected to each well and reacted with shaking at room temperature for one hour. After completion of reaction, the plate was washed five times with a washing solution, and a TMB color developer solution (product of Scy Tek Laboratories) (100 μL/well) was injected to the wells, followed by reaction at room temperature for 30 minutes. A reaction terminator solution (product of Scy Tek Laboratories) (100 μL/well) was added to the wells to terminate the reaction, and absorbance at 450 nm was measured by means of a microplate reader.

As a result, the new assay system provided excellent percent recovery in a concentration range from low to high. In contrast, the conventional assay system provided low percent recovery at low concentration (Table 3). In the reproducibility test, the new assay system provided excellent CV values, whereas the conventional assay system provided higher CV values at low PTX3 concentration, particularly in the case where no PTX3 had been added (Table 4). Therefore, the newly developed assay system has realized high-sensitivity and high-accuracy.

TABLE 3

Comparison of the assay system of the present invention with the conventional assay system (addition-recovery test)

| | Conventional assay system | | | | New assay system | | | |
|---|---|---|---|---|---|---|---|---|
| Samples | Endogenous PTX3 (ng/mL) | Added PTX3 (ng/mL) | Concentration measured (ng/mL) | Percent recovery (%) | Endogenous PTX3 (ng/mL) | Added PTX3 (ng/mL) | Concentration measured (ng/mL) | Percent recovery (%) |
| 1 | 0.8 | 2.00 | 2.8 | 85 | 1.5 | 2.00 | 3.6 | 97 |
| | | 5.00 | 5.4 | 78 | | 5.00 | 6.5 | 106 |
| | | 10.00 | 9.9 | 87 | | 10.00 | 11.0 | 105 |
| 2 | 1.4 | 2.00 | 3.5 | 90 | 2.5 | 2.00 | 4.4 | 87 |
| | | 5.00 | 6.4 | 85 | | 5.00 | 7.2 | 98 |
| | | 10.00 | 11.5 | 96 | | 10.00 | 11.9 | 103 |
| 3 | 1.1 | 2.00 | 3.1 | 89 | 1.6 | 2.00 | 3.6 | 93 |
| | | 5.00 | 6.5 | 92 | | 5.00 | 6.6 | 106 |
| | | 10.00 | 12.1 | 106 | | 10.00 | 11.4 | 108 |
| 4 | 0.6 | 2.00 | 2.4 | 78 | 0.7 | 2.00 | 2.8 | 95 |
| | | 5.00 | 5.5 | 85 | | 5.00 | 5.6 | 103 |
| | | 10.00 | 11.3 | 103 | | 10.00 | 10.3 | 106 |
| 5 | 1.9 | 2.00 | 3.6 | 75 | 2.2 | 2.00 | 4.3 | 92 |
| | | 5.00 | 6.2 | 73 | | 5.00 | 6.6 | 92 |
| | | 10.00 | 10.44 | 82 | | 10.00 | 11.0 | 95 |
| 6 | 1.4 | 2.00 | 3.3 | 83 | 1.6 | 2.00 | 3.6 | 86 |
| | | 5.00 | 6.7 | 92 | | 5.00 | 6.1 | 96 |
| | | 10.00 | 11.8 | 100 | | 10.00 | 11.1 | 104 |
| 7 | 0.8 | 2.00 | 2.8 | 85 | 1.5 | 2.00 | 3.5 | 84 |
| | | 5.00 | 5.7 | 83 | | 5.00 | 6.1 | 97 |
| | | 10.00 | 10.8 | 95 | | 10.00 | 10.1 | 94 |
| 8 | 1.1 | 2.00 | 3.0 | 79 | 1.5 | 2.00 | 3.4 | 83 |
| | | 5.00 | 5.9 | 82 | | 5.00 | 6.1 | 98 |
| | | 10.00 | 10.0 | 85 | | 10.00 | 10.7 | 101 |

TABLE 4

| | | Conventional assay system (absorbance) | | | New assay system (absorbance) | | |
|---|---|---|---|---|---|---|---|
| Samples | | Mean | SD | CV (%) | Mean | SD | CV (%) |
| Standard substance (recombinant PTX3) | 0 ng/mL | 0.014 | 0.00141 | 10.1 | 0.013 | 0.00055 | 4.3 |
| | 0.125 ng/mL | 0.037 | 0.00281 | 7.6 | 0.035 | 0.00071 | 2.0 |
| | 0.25 ng/mL | 0.063 | 0.00191 | 3.0 | 0.055 | 0.00084 | 1.5 |
| | 1 ng/mL | 0.184 | 0.00636 | 3.5 | 0.174 | 0.00148 | 0.9 |
| | 4 ng/mL | 0.634 | 0.05162 | 8.1 | 0.623 | 0.00592 | 0.9 |
| | 10 ng/mL | 1.446 | 0.07283 | 5.0 | 1.430 | 0.01841 | 1.3 |
| | 16 ng/mL | 2.327 | 0.02263 | 1.0 | 2.172 | 0.01736 | 0.8 |
| Plasma samples from healthy subjects | 1 | 0.147 | 0.00483 | 3.3 | 0.124 | 0.00195 | 1.6 |
| | 2 | 0.142 | 0.00636 | 4.5 | 0.124 | 0.00207 | 1.7 |
| | 3 | 0.130 | 0.00354 | 2.7 | 0.108 | 0.00217 | 2.0 |
| | 4 | 0.282 | 0.00424 | 1.5 | 0.226 | 0.00336 | 1.5 |
| | 5 | 0.269 | 0.01485 | 5.5 | 0.224 | 0.00385 | 1.7 |
| | 6 | 0.145 | 0.00441 | 3.0 | 0.115 | 0.00365 | 3.2 |
| Plasma samples from angina patients | 1 | 0.737 | 0.02831 | 3.8 | 0.594 | 0.00646 | 1.1 |
| | 2 | 0.988 | 0.02242 | 2.3 | 0.825 | 0.00466 | 0.6 |

Example 21

Determination of Blood PTX3 Level in Heart Disease Patients

Blood PTX3 level of healthy people was compared with that of subjects suffering heart disease. The assayed samples were as follows: 92 plasma samples obtained from peripheral blood of healthy people not suffering any disease under treatment (normal group); 31 plasma samples obtained from the coronary artery of heart disease patients complaining of chest pain (although they complained of chest pain and were suspected of angina on the basis of symptoms and results of a load ECG test and a load myocardial scintillation test, arteriosclerosis was not observed in coronary imaging, and the suspicion of angina was denied by a cardiovascular internal medicine specialist) (chest pain group); and 24 plasma samples obtained from the coronary artery of stable angina patients (stable angina group). These samples were assayed by means of the new assay kit produced in Example 18.

Specifically, a sample dilution buffer (100 µL/well) was injected to wells of an antibody-immobilized plate, and a standard sample or each test sample (10 µL) was injected to the wells, and reacted with shaking reaction at room temperature for one hour. Subsequently, the plate was washed five times with a washing solution (PBS, 0.05% Tween 20), and a labeled antibody solution (100 µL) was injected to each well and reacted with shaking at room temperature for one hour. After completion of reaction, the plate was washed five times, and a TMB color developer solution (product of Scy Tek Laboratories) (100 µL/well) was injected to the wells, followed by reaction at room temperature for 30 minutes. A reaction terminator solution (product of Scy Tek Laboratories) (100 µL/well) was added to the wells to terminate the reaction, and absorbance at 450 nm was measured by means of a microplate reader.

Figure 13:
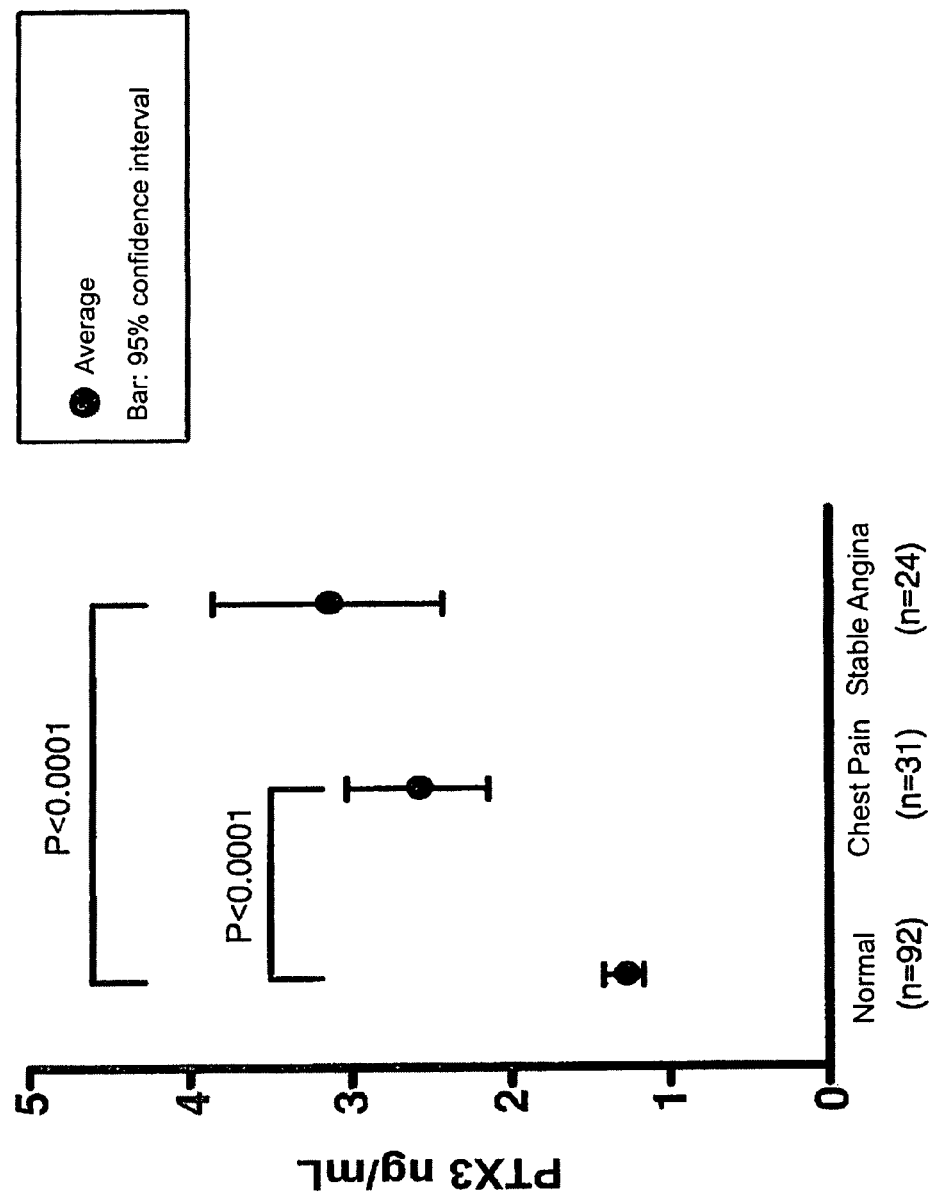
[FIG. 13] Comparison of blood PTX3 level between healthy subjects and heart disease patients.

As a result, the average PTX3 blood level of the normal group was found to be 1.27 ng/mL, that of the chest pain group 2.57 ng/mL, and that of the stable angina group 3.13 ng/mL. Thus, significant difference (p<0.0001) was observed between the normal group and the chest pain group, and between the normal group and the stable angina group (FIG. 13).

Therefore, the severity of vasculopathy can be determined as mild through a blood PTX3 level assay by use of the anti-PTX3 monoclonal antibody of the present invention.

Example 22

Figure 14:
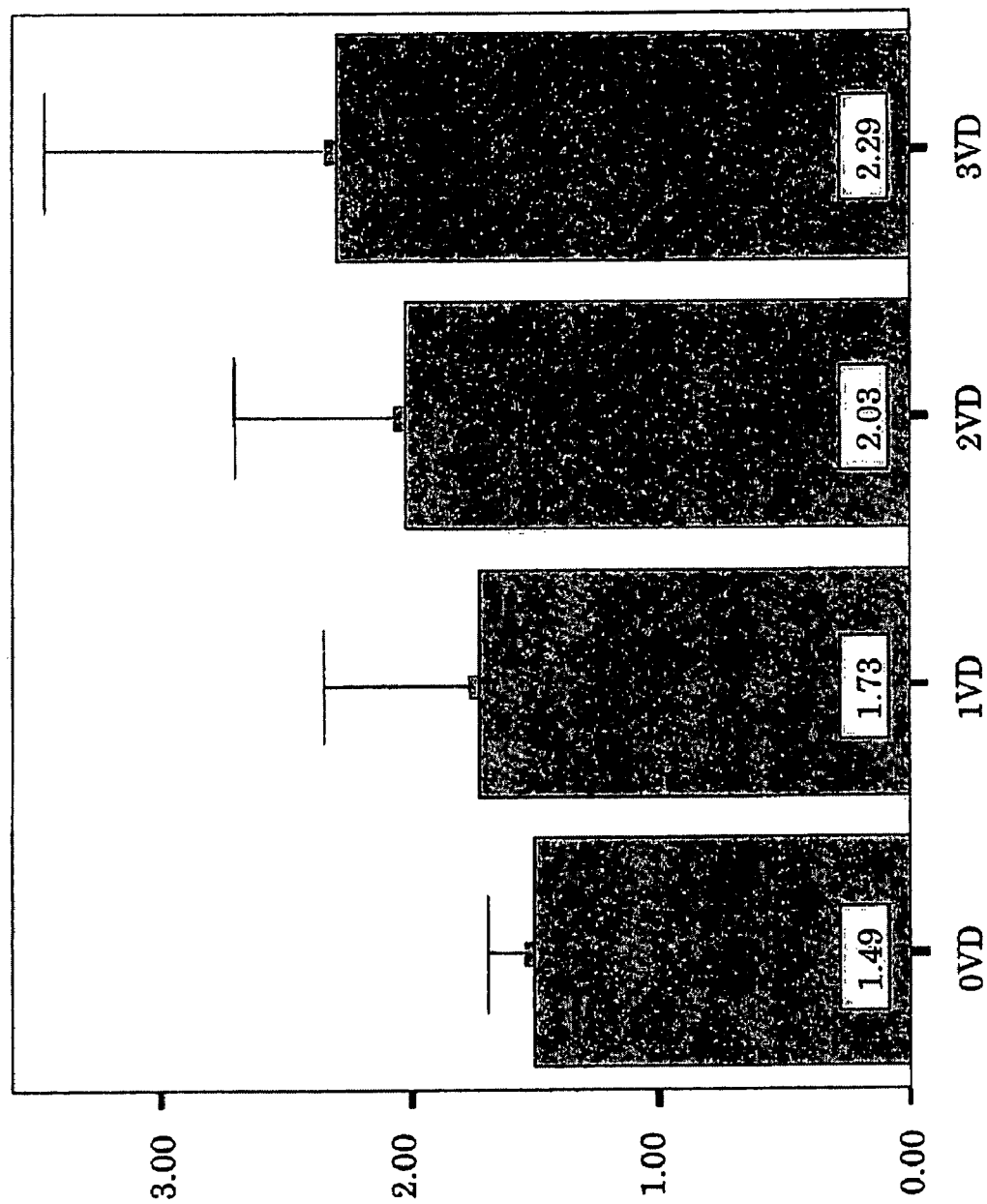
[FIG. 14] Relationship between the number of diseased coronary arteries and blood PTX3 level.

Relationship Between Blood PTX3 Level and the Number of Diseased Coronary Arteries The relationship between blood PTX3 level and the severity of heart disease was investigated through determining blood PTX3 level of heart disease patients by means of the new assay kit produced in Example 18. The samples assayed in the study were as follows: 44 plasma samples obtained from peripheral blood of people diagnosed as having no coronary lesion (0VD); 15 plasma samples obtained from patients in which one diseased coronary arteries (1 VD); 22 plasma samples obtained from patients in which two diseased coronary arteries (2 VD); and 11 plasma samples obtained from patients in which three diseased coronary arteries (3 VD). PTX3 assay of these samples were performed through the assay method as employed in Example 17. As a result, the average blood PTX3 level of the group 0 VD was found to be 1.49 ng/mL, that of the group 1 VD 1.73 ng/mL, that of the group 2 VD 2.03 ng/mL, and that of the group 3 VD 2.29 ng/mL. Thus, significant difference was observed between the groups 0 VD and 2 VD (P=0.05), and between the groups 0 VD and 3 VD (P=0.01) (FIG. 14).

Therefore, as the higher the blood PTX3 level was observed by use of the anti-PTX3 monoclonal antibody of the present invention, the severity of a heart disease such as coronary lesion was found to be more serious.

---

The invention claimed is:

1. A method of determining the severity of mild vasculopathy, comprising measuring PTX3 level in an assay sample by use of an anti-PTX3 monoclonal antibody;
wherein said anti-PTX3 monoclonal antibody is produced by hybridoma PPMX 0104 (FERM BP-10719) or hybridoma PPMX 0105 (FERM BP-10720).

2. The method as described in claim 1, wherein the mild vasculopathy is associated with a heart disease or a cerebral disease.

3. The method as described in claim 2, wherein the mild vasculopathy associated with a heart disease is a coronary artery disease.

4. The method of claim 1, wherein the assay sample is blood, serum or plasma.

5. The method of claim 1, wherein the anti-PTX3 monoclonal antibody is immobilized on a support and the anti-PTX3 monoclonal antibody is labeled with a labeling substance.

6. The method of claim 1, wherein the anti-PTX3 monoclonal antibody or a binding fragment thereof recognizes a conformational epitope of PTX3.

7. The method of claim 1, wherein the anti-PTX3 monoclonal antibody is produced from PPMX 0104 (FERM BP-10719).

8. A diagnostic agent for determining the severity of mild vasculopathy, containing an anti-PTX3 monoclonal antibody or a binding fragment thereof;
wherein said anti-PTX3 monoclonal antibody is produced by hybridoma PPMX 0104 (FERM BP-10719) or hybridoma PPMX 0105 (FERM BP-10720).

9. The diagnostic agent as described in claim 8, wherein the anti-PTX3 monoclonal antibody is immobilized on a support and the anti-PTX3 monoclonal antibody is labeled with a labeling substance.

10. The diagnostic agent of claim 8, wherein the anti-PTX3 monoclonal antibody recognizes a conformational epitope of PTX3.

11. The diagnostic agent as described in claim 10, wherein the anti-PTX3 monoclonal antibody is produced by PPMX 0104 (FERM BP-10719).

12. An anti-PTX3 monoclonal antibody or a binding fragment thereof, recognizing a conformational epitope of PTX3;
wherein said anti-PTX3 monoclonal antibody is produced by hybridoma PPMX 0104 (FERM BP-10719) or hybridoma PPMX 0105 (FERM BP-10720).

13. The anti-PTX3 monoclonal antibody or a binding fragment thereof as described in claim 12, wherein the antibody is produced by hydridoma PPMX 0104 (FERM BP-10719).

14. A hydridoma which produces an anti-PTX3 monoclonal antibody recognizing a conformational epitope of PTX3;
wherein the hybridoma is hybridoma PPMX 0104 (FERM BP-10719) or hybridoma PPMX 0105 (FERM BP-10720).

15. The hybridoma as described in claim 14, which is PPMX 0104 (FERM BP-10719).

16. The hybridoma as described in claim 14, which is hybridoma PPMX 0105 (FERM BP-10720).

17. An isolated or purified monoclonal antibody produced by hybridoma PPMX 0104 (FERM BP-10719), or an antigen-binding fragment thereof.

18. An isolated or purified monoclonal antibody produced by hybridoma PPMX 0105 (FERM BP-10720), or an antigen-binding fragment thereof.

19. A kit comprising:
the isolated or purified antibody claim 17 or an antigen-binding fragment thereof;
a solid support, and optionally,
at least one component selected from the group consisting of a blocking solution, reaction solution, reaction-terminating solution, or one or more reagents for treating a sample.

20. A kit comprising:
the isolated or purified antibody of claim 18 or an antigen-binding fragment thereof;
a solid support, and optionally,
at least one component selected from the group consisting of a blocking solution, reaction solution, reaction-terminating solution, or one or more reagents for treating a sample.

* * * * *

UNITED STATES PATENT AND TRADEMARK OFFICE
CERTIFICATE OF CORRECTION

PATENT NO. : 7,955,807 B2
APPLICATION NO. : 12/092272
DATED : June 7, 2011
INVENTOR(S) : Tatsuhiko Kodama et al.

It is certified that error appears in the above-identified patent and that said Letters Patent is hereby corrected as shown below:

Column 32, Line 26, "A kit comprising: the isolated or purified antibody claim 17" should read -- A kit comprising: the isolated or purified antibody of claim 17--

Signed and Sealed this
Twenty-fifth Day of October, 2011

David J. Kappos
*Director of the United States Patent and Trademark Office*

SEQUENCE LISTING

<160> NUMBER OF SEQ ID NOS: 6

<210> SEQ ID NO 1
<211> LENGTH: 1146
<212> TYPE: DNA
<213> ORGANISM: Homo sapiens

<400> SEQUENCE: 1

```
atgcatctcc ttgcgattct gttttgtgct ctctggtctg cagtgttggc cgagaactcg      60
gatgattatg atctcatgta tgtgaatttg gacaacgaaa tagacaatgg actccatccc     120
actgaggacc ccacgccgtg cgactgcggt caggagcact cggaatggga caagctcttc     180
atcatgctgg agaactcgca gatgagagag cgcatgctgc tgcaagccac ggacgacgtc     240
ctgcggggcg agctgcagag gctgcgggag gagctgggcc ggctcgcgga aagcctggcg     300
aggccgtgcg cgccgggggc tcccgcagag gccaggctga ccagtgctct ggacgagctg     360
ctgcaggcga cccgcgacgc gggccgcagg ctggcgcgta tggagggcgc ggaggcgcag     420
cgcccagagg aggcggggcg cgcccctggcc gcggtgctag aggagctgcg gcagacgcga     480
gccgacctgc acgcggtgca gggctgggct gcccggagct ggctgccggc aggttgtgaa     540
acagctattt tattcccaat gcgttccaag aagattttg gaagcgtgca tccagtgaga     600
```

-continued

```
ccaatgaggc ttgagtcttt tagtgcctgc atttgggtca aagccacaga tgtattaaac      660
aaaaccatcc tgttttccta tggcacaaag aggaatccat atgaaatcca gctgtatctc      720
agctaccaat ccatagtgtt tgtggtgggt ggagaggaga acaaactggt tgctgaagcc      780
atggtttccc tggaaggtg gacccacctg tgcggcacct ggaattcaga ggaagggctc       840
acatccttgt gggtaaatgg tgaactggcg gctaccactg ttgagatggc cacaggtcac      900
attgttcctg agggaggaat cctgcagatt ggccaagaaa agaatggctg ctgtgtgggt      960
ggtggctttg atgaaacatt agccttctct gggagactca caggcttcaa tatctgggat     1020
agtgttctta gcaatgaaga gataagagag accggaggag cagagtcttg tcacatccgg     1080
gggaatattg ttgggtgggg agtcacagag atccagccac atggaggagc tcagtatgtt     1140
tcataa                                                                1146
```

<210> SEQ ID NO 2
<211> LENGTH: 381
<212> TYPE: PRT
<213> ORGANISM: Homo sapiens

<400> SEQUENCE: 2

```
Met His Leu Leu Ala Ile Leu Phe Cys Ala Leu Trp Ser Ala Val Leu
1               5                   10                  15

Ala Glu Asn Ser Asp Asp Tyr Asp Leu Met Tyr Val Asn Leu Asp Asn
            20                  25                  30

Glu Ile Asp Asn Gly Leu His Pro Thr Glu Asp Pro Thr Pro Cys Asp
        35                  40                  45

Cys Gly Gln Glu His Ser Glu Trp Asp Lys Leu Phe Ile Met Leu Glu
    50                  55                  60

Asn Ser Gln Met Arg Glu Arg Met Leu Leu Gln Ala Thr Asp Asp Val
65                  70                  75                  80

Leu Arg Gly Glu Leu Gln Arg Leu Arg Glu Glu Leu Gly Arg Leu Ala
                85                  90                  95

Glu Ser Leu Ala Arg Pro Cys Ala Pro Gly Ala Pro Ala Glu Ala Arg
            100                 105                 110

Leu Thr Ser Ala Leu Asp Glu Leu Leu Gln Ala Thr Arg Asp Ala Gly
        115                 120                 125

Arg Arg Leu Ala Arg Met Glu Gly Ala Glu Ala Gln Arg Pro Glu Glu
    130                 135                 140

Ala Gly Arg Ala Leu Ala Ala Val Leu Glu Glu Leu Arg Gln Thr Arg
145                 150                 155                 160

Ala Asp Leu His Ala Val Gln Gly Trp Ala Ala Arg Ser Trp Leu Pro
                165                 170                 175

Ala Gly Cys Glu Thr Ala Ile Leu Phe Pro Met Arg Ser Lys Lys Ile
            180                 185                 190

Phe Gly Ser Val His Pro Val Arg Pro Met Arg Leu Glu Ser Phe Ser
        195                 200                 205

Ala Cys Ile Trp Val Lys Ala Thr Asp Val Leu Asn Lys Thr Ile Leu
    210                 215                 220

Phe Ser Tyr Gly Thr Lys Arg Asn Pro Tyr Glu Ile Gln Leu Tyr Leu
225                 230                 235                 240

Ser Tyr Gln Ser Ile Val Phe Val Val Gly Gly Glu Glu Asn Lys Leu
                245                 250                 255

Val Ala Glu Ala Met Val Ser Leu Gly Arg Trp Thr His Leu Cys Gly
            260                 265                 270

Thr Trp Asn Ser Glu Glu Gly Leu Thr Ser Leu Trp Val Asn Gly Glu
```

```
                275                 280                 285
Leu Ala Ala Thr Thr Val Glu Met Ala Thr Gly His Ile Val Pro Glu
    290                 295                 300

Gly Gly Ile Leu Gln Ile Gly Gln Glu Lys Asn Gly Cys Cys Val Gly
305                 310                 315                 320

Gly Gly Phe Asp Glu Thr Leu Ala Phe Ser Gly Arg Leu Thr Gly Phe
                325                 330                 335

Asn Ile Trp Asp Ser Val Leu Ser Asn Glu Glu Ile Arg Glu Thr Gly
            340                 345                 350

Gly Ala Glu Ser Cys His Ile Arg Gly Asn Ile Val Gly Trp Gly Val
        355                 360                 365

Thr Glu Ile Gln Pro His Gly Gly Ala Gln Tyr Val Ser
    370                 375                 380

<210> SEQ ID NO 3
<211> LENGTH: 30
<212> TYPE: DNA
<213> ORGANISM: Artificial Sequence
<220> FEATURE:
<223> OTHER INFORMATION: Primer sequence for amplification of NM_002852

<400> SEQUENCE: 3
cggggtatgc atctccttgc gattctgttt                                       30

<210> SEQ ID NO 4
<211> LENGTH: 38
<212> TYPE: DNA
<213> ORGANISM: Artificial Sequence
<220> FEATURE:
<223> OTHER INFORMATION: Primer sequence for amplification of NM_002852

<400> SEQUENCE: 4
cgcggatcct tatgaaacat actgagctcc tccatgtg                              38

<210> SEQ ID NO 5
<211> LENGTH: 30
<212> TYPE: DNA
<213> ORGANISM: Artificial Sequence
<220> FEATURE:
<223> OTHER INFORMATION: Primer sequence for amplification of NM_002852

<400> SEQUENCE: 5
atgcatctcc ttgcgattct gttttgtgct                                       30

<210> SEQ ID NO 6
<211> LENGTH: 29
<212> TYPE: DNA
<213> ORGANISM: Artificial Sequence
<220> FEATURE:
<223> OTHER INFORMATION: Primer sequence for amplification of NM_002852

<400> SEQUENCE: 6
ccagctccgg gcagcccagc cctgcaccg                                        29
```